(12) United States Patent
Rostaing et al.

(10) Patent No.: US 10,856,854 B2
(45) Date of Patent: Dec. 8, 2020

(54) DEVICE FOR OBTAINING BIOLOGICAL MATERIAL AND/OR BIOLOGICAL INFORMATION FROM A SAMPLE WITH A HETEROGENEOUS MATRIX

(71) Applicant: BIOMÉRIEUX, Marcy-l'Etoile (FR)

(72) Inventors: Hervé Rostaing, Le Versoud (FR); Agnès Dupont-Filliard, Les Adrets (FR); Sandrine Gicquel, Grenoble (FR); Carole Vachon, St. Etienne de Crossey (FR); Patrick Broyer, Saint Cassien (FR); Jérôme Blaze, La Terrasse (FR)

(73) Assignee: BIOMERIEUX, Marcy-l'Etoile (FR)

( * ) Notice: Subject to any disclaimer, the term of this patent is extended or adjusted under 35 U.S.C. 154(b) by 452 days.

(21) Appl. No.: 15/507,187

(22) PCT Filed: Aug. 28, 2015

(86) PCT No.: PCT/FR2015/052292
§ 371 (c)(1),
(2) Date: Feb. 27, 2017

(87) PCT Pub. No.: WO2016/030642
PCT Pub. Date: Mar. 3, 2016

(65) Prior Publication Data
US 2017/0273670 A1    Sep. 28, 2017

(30) Foreign Application Priority Data
Aug. 29, 2014   (FR) ..................................... 14 58143

(51) Int. Cl.
*A61B 10/00* (2006.01)
*C12M 1/12* (2006.01)
(Continued)

(52) U.S. Cl.
CPC ........... *A61B 10/0038* (2013.01); *C12M 1/12* (2013.01); *C12M 1/28* (2013.01); *G01N 1/08* (2013.01); *G01N 33/483* (2013.01)

(58) Field of Classification Search
CPC ............................ A61B 10/0038; C12M 1/12
(Continued)

(56) References Cited

U.S. PATENT DOCUMENTS

| 4,081,356 A | * | 3/1978 | Zierdt ................ A61B 10/0038 |
| | | | 209/17 |
| 4,735,905 A | | 4/1988 | Parker |

(Continued)

FOREIGN PATENT DOCUMENTS

| EP | 1 656 887 | | 5/2006 |
| WO | WO 03/014705 | * | 2/2003 |
| WO | WO2003014705 | | 2/2003 |

OTHER PUBLICATIONS

Srijan, A., et al., "Field Evaluation of a Transport Medium and Enrichment Broth for Isolation of *Campylobacter* Species from Human Diarrheal Stool Samples", Open Journal of Medical Microbiology, vol. 3 (2013), pp. 48-52.

(Continued)

*Primary Examiner* — Matthew D Krcha
*Assistant Examiner* — Jacqueline Brazin
(74) *Attorney, Agent, or Firm* — Oliff PLC

(57) ABSTRACT

The invention relates to a device for obtaining biological material and/or biological information from a sample with a heterogeneous matrix, to the uses of said device, to methods implementing said device, and to kits for obtaining biological material and/or biological information from a sample with a heterogeneous matrix, comprising the different constituents of said device.

46 Claims, 15 Drawing Sheets

(51) Int. Cl.
*C12M 1/28* (2006.01)
*G01N 1/08* (2006.01)
*G01N 33/483* (2006.01)

(58) Field of Classification Search
USPC .......................................................... 422/557
See application file for complete search history.

(56) References Cited

U.S. PATENT DOCUMENTS

| | | | | |
|---|---|---|---|---|
| 5,730,147 | A * | 3/1998 | Craig | A61B 10/0038 |
| | | | | 374/E13.002 |
| 8,486,353 | B2 * | 7/2013 | Wu | A61B 10/007 |
| | | | | 422/557 |
| 2006/0115385 | A1 * | 6/2006 | Jon Meyer | A61B 10/0096 |
| | | | | 422/547 |
| 2006/0147348 | A1 * | 7/2006 | Liang | A61B 10/0045 |
| | | | | 422/400 |
| 2008/0223815 | A1 * | 9/2008 | Konrad | B01L 3/50825 |
| | | | | 215/329 |
| 2011/0048981 | A1 | 3/2011 | Okumura et al. | |
| 2014/0161688 | A1 * | 6/2014 | Campton | B01L 3/5021 |
| | | | | 422/533 |

OTHER PUBLICATIONS

Wasfy, M., et al., "Comparison of Preservation Media for Storage of Stool Samples", Journal of Clinical Microbiology, vol. 33, No. 8 (Aug. 1995), pp. 2176-2178.

Written Opinion for PCT/FR2015/052292, issued by the International Searching Authority (including English translation).

International Search Report of the International Searching Authority dated Nov. 30, 2015 (including English translation) for PCT/FR2015/052292.

* cited by examiner

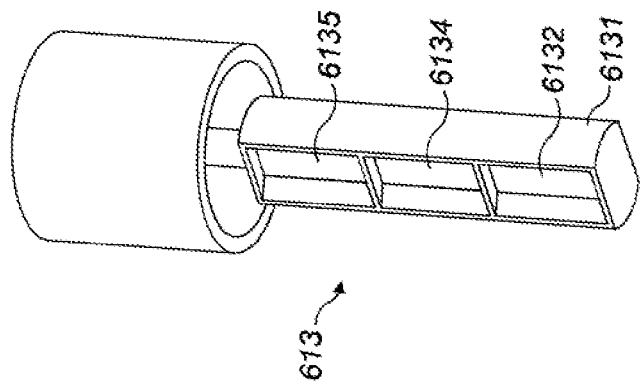
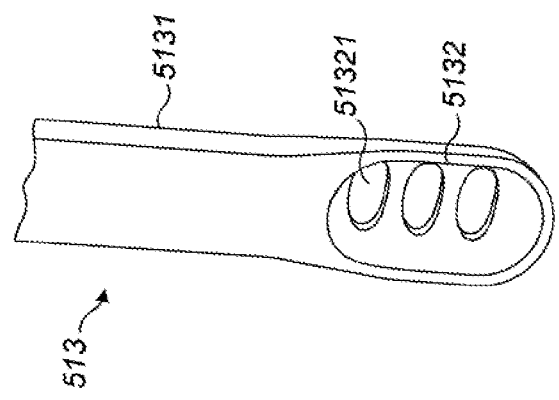
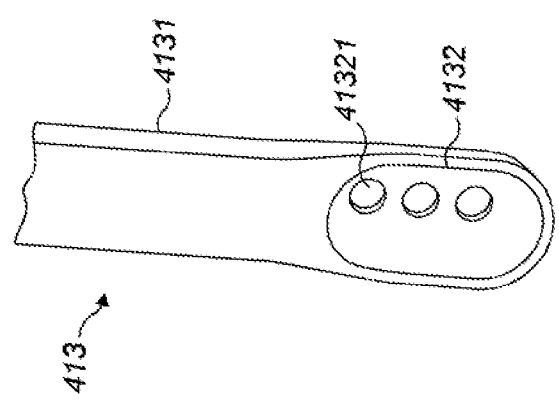

DEVICE FOR OBTAINING BIOLOGICAL MATERIAL AND/OR BIOLOGICAL INFORMATION FROM A SAMPLE WITH A HETEROGENEOUS MATRIX

This application is a National Stage application of International Application No. PCT/FR2015/052292 filed Aug. 28, 2015. This application also claims priority under 35 U.S.C. § 119 to FR Patent Application No. 1458143, filed Aug. 29, 2014.

TECHNICAL FIELD

The present invention relates to the field of obtaining biological material and/or biological information from a sample with a heterogeneous matrix for the purposes of subsequent analyses, in particular for diagnostic purposes.

PRIOR ART

The testing of biological material and/or biological information from samples of various origins (for example of industrial, food-processing or clinical origin) requires the implementation of techniques which allow detection—for example for the purposes of identifying and/or counting microorganisms—and the yield of which in terms of results must be as efficient as possible. Generally, if said biological material is considered, the latter may be of non-pathogenic nature. However, in the diagnostic field, the biological material which is the subject of testing is usually pathogenic, consequently requiring rapid and precise detection thereof in order to initiate corrective actions ad hoc as soon as possible. Quite obviously, the toxins and other metabolites produced by this pathogenic biological material can also be investigated.

In standard fashion, the detection of biological material and/or biological information can be carried out by means of immunological assays, enzymatic assays, molecular biology techniques, or else, as regards said biological material, by counting and/or identification on a culture dish. In any event, whether it is a question of biological material and/or of biological information, the detection sensitivity and the detection specificity are two important factors for evaluating the efficiency of the test performed.

By way of example, the detection of microorganisms is conventionally carried out on selective culture media plated out on a Petri dish, as recommended by the standards of ISO (International Organization for Standardization) type or the BAM-FDA (Bacteriological Analytical Manual of the Food and Drug Administration) methods. These standards recommend in particular the use of media such as polymyxin egg yolk mannitol bromothymol blue Agar (the acronym of which is PEMBA) or mannitol-egg yolk-polymyxin Agar (the acronym of which is MYP). The identification of microorganisms is conventionally carried out according to morphological, culture and/or metabolic criteria. Nevertheless, these methods of detection on a Petri dish can be negatively affected by the presence of non-specific elements, derived from the sample to be analyzed. This is particularly true with regard to samples with a heterogeneous matrix, namely samples which have differences in terms of consistency (solid particles, parts that are more or less liquid, semi-solid parts, etc.), such as soil, human or animal stool, phlegm or sputum samples or else tissue samples (medico-legal samples), which are generally rich in polysaccharides, cell debris, and inhibitors of all types (bile salt, polyphenols, polysaccharide, fibers, hemoglobin, etc.), capable of disrupting the growth of the microorganisms sought and thus of giving rise to false-negative results (detection sensitivity problem).

Alternatively, the detection of biological information derived from the biological material can be carried out, for example, using conventional methods for amplifying nucleic acids, specific for one or more types of microorganisms and viruses that are sought. However, these techniques are sensitive and may be significantly inhibited by compounds such as polysaccharides, cell debris and inhibitors of all types. This can result in the obtaining of false-negative results (detection sensitivity problems) or in an incorrect diagnosis and can have serious consequences for the human or animal patient. Consequently, it is essential to isolate the microorganisms and/or the viruses such that a minimum number of inhibitors are present in the isolate. This is particularly important for samples with a heterogeneous matrix, as previously mentioned. This is because said samples comprise a large number of non-specific constituents (polysaccharides, cell debris, inhibitors of all types), capable of generating false negatives during the implementation of the abovementioned nucleic acid amplification methods.

In addition, and regardless of the type of detection method used, these samples with a heterogeneous matrix have, in addition to the conventional problems of contamination of the sample and/or of the environment, more specific problems with respect to metering out/calibration (correlation difficult between amount of the sample taken and mass thereof, means of calibration constant from one sample to the other) and with respect to suspending in a liquid medium, that are inherent in the nature of the sample.

Currently, various methods for analyzing the genetic material contained in a sample with a heterogeneous matrix exist. By way of example, the "QIAamp® DNA" kit from the company QiaGen makes it possible to isolate and purify the total genomic DNA of a solid or liquid sample (such as blood, serum, plasma, etc.). This kit uses a device consisting of filtration columns and tubes suitable for use with standard microcentrifuges. According to the supplier's recommendations, the method for obtaining the total genomic DNA comprises the following steps: taking a given amount of the sample of interest (by weighing) depending on its nature, introducing said sample into a tube containing a solution for suspending it, placing the sample in suspension by means of vigorous stirring of vortex type. Once the sample has been vigorously mixed, a lysis solution is added and an incubation step is carried out for several minutes, in order to break the cell membranes and to release the genetic information into the solution. Next, in order to remove the debris, the solution is centrifuged and the supernatant is removed. There are subsequently laborious steps of adding solutions and performing centrifugations which make it possible to purify the DNA sample, before eluting it on a column by centrifugation.

However, this method, using the abovementioned "QIAamp® DNA" kit, has several drawbacks, in particular when the sample tested is a sample with a heterogeneous matrix. This is because the first steps of weighing and transferring the sample into the microcentrifuge tubes are critical owing to the narrowness of the opening of said tubes. This transfer can thus prove to be difficult and can require additional handling and equipment, and extended implementation times. In addition, during these weighing and/or transfer operations, there is a significant risk of:

loss of the material, contamination of the sample and/or of the environment and/or of the laboratory technician, discomfort of the laboratory technician associated with the repeated handling of samples of stool, sputum or phlegm type, difficulty in calibrating the sample by weighing.

Moreover, the numerous steps constituting the protocol of the "QIAamp® DNA" kit, which involve the handling of a considerable amount of different tubes, are capable of causing handling errors. Furthermore, the handling of small tubes, such as tubes suitable for microcentrifuges, does not prove to be very practical for the laboratory technician, and is therefore also capable of giving rise to losses in terms of time and efficiency. In addition, the "QIAamp® DNA" kit enables only the isolation of nucleic acid from a sample, and does not make it possible to detect the presence of viable microorganisms, for instance detection on culture medium. Furthermore, the "QIAamp® DNA" kit does not enable the detection of yeast from a stool sample.

In another example, patent U.S. Pat. No. 4,081,356 describes a device and a method for recovering small sediments containing parasite eggs and larvae from a sample of fecal material. The device disclosed consists of two compartments separated by a basic (namely not very selective) filtration element, such as a filter and a steel mesh; the upper compartment being obstructed at its external end by a spatula enabling the taking of a sample. The sample of fecal material is taken by means of the spatula, which is suitable for being connected to the upper part of the compartment. Next, the sample is emulsified using a solution of formaldehyde, optionally supplemented with a surfactant, mechanically by means of a rod. The emulsification is finalized by a step of horizontal agitation in the presence of glass beads. A vertical agitation step then makes it possible to pass the entire emulsified sample into the lower compartment of the device, through the basic filtration element. Ether is then used to rinse this basic filtration element and to allow the formation of a mixture in the lower compartment. Finally, the lower compartment is agitated and centrifuged to separate the resulting mixture into various layers of materials of different densities, in order to isolate the layer of sediment containing the parasite eggs and the larvae.

However, the device used in the abovementioned method has several drawbacks, in particular associated with the flagrant lack of selectivity of the basic filtration element, which allows the passage, in addition to the abovementioned eggs and larvae, of non-specific elements that will subsequently sediment in various layers. Moreover, the first steps of taking the sample, in particular the step of connecting the spatula to the upper compartment, do not allow clean and easy taking of a sample and, consequently, require additional handlings and extended implementation times. Furthermore, this inevitably affects the reproducibility of the method using this device, insofar as it proves to be extremely difficult—or even impossible—to take a precise and calibrated volume of said sample, in particular from hard stools of type 1 and 2 on the Bristol scale. Human stools are commonly characterized and classified according to the Bristol scale consisting of a visual classification which divides human stools up into seven types. Types 1-2 correspond to hard stools, types 3-4 are considered to be normal, and types 5-6-7 correspond to stools of liquid consistency.

In view of the problems presented above, an objective of the present invention aims to develop a device and the process(es) associated therewith making it possible:

to meter out/calibrate the amount of sample with a heterogeneous matrix that is taken without needing to weigh the latter, to efficiently suspend said sample in a liquid medium, to limit the problems associated with clogging (obstruction) of the filters in order to facilitate filtration and to improve recovery of the biological material and/or of the biological information, to limit the obtaining of non-specific elements capable of distorting the result of the analysis in fine, to prevent the loss of a part of the sample during the sample transfer into the container (for example into the tube), to improve the efficiency and practicality, to limit as much as possible the risks of contamination of the sample and/or of the environment and/or of the laboratory technician, to simplify the protocol for preparing samples with a heterogeneous matrix in order to reduce the operating time, the number of materials and consumables used, and the risks of errors and to improve the reproducibility, to propose a device compatible with all of the known analytical methods (microbiology, culture, virology, bacteriology, immunoassay, metasequencing, PCR, etc.), to isolate yeasts.

Other objectives will emerge, as appropriate, on reading the present patent application.

SUMMARY OF THE INVENTION

Consequently, the subject of the present invention relates to a device for obtaining biological material and/or biological information from a sample with a heterogeneous matrix, for example a human or animal stool (feces) sample, said device comprising:

a container suitable for receiving a content comprising said sample and at least one suspending solution, intended to enable said sample to be placed in suspension, a stopper which makes it possible to close said container, preferably hermetically, said stopper comprising:

at least one calibrated sampling means, which makes it possible to take a predetermined volume of said sample corresponding to a given mass, said sampling means comprising at least one calibrated hollow part connected to the internal part of the stopper and extending from said internal part of the stopper to the inside of the container when said stopper and said container are assembled, at least one opening, which can preferably be closed by a removable closure means, allowing communication of fluid between the interior of said container and the exterior of said device when said stopper and said container are assembled, at least one filtration means, positioned with respect to said opening in such a way as to filter the content while said content passes from the interior of said container to the exterior of said device via said opening, said filtration means being suitable for allowing the selective passage of said biological material and/or biological information to the exterior of said device.

Thus, the device according to the invention makes it possible to simplify and facilitate the taking of a given mass of a sample with a heterogeneous matrix (in particular while dispensing with a difficult weighing step), the placing of said sample in suspension and the isolation of the biological material and/or of the biological information that it contains, with a view to the subsequent analysis thereof. In particular, the device according to the invention has the advantage of being suitable for treating samples with a heterogeneous matrix having a very varied consistency and/or texture.

The simplification of the isolation of the biological material and/or of the biological information obtained by virtue of the device according to the invention leads in particular to a decrease in the "open tube" steps, which require consumables and technical manipulations (pipetting, removal of supernatant, centrifugation, etc.), capable of generating errors and contaminations of the sample and/or of the outside environment. The device according to the invention also makes it possible to dispense with the use of multiple pieces of equipment, such as balances, bead beaters or centrifuges.

The term "sample with a heterogeneous matrix" is intended to mean a small part or a small amount isolated from a material with a heterogeneous matrix, for analysis. The material with a heterogeneous matrix from which the sample is taken is characterized by intrinsic differences in terms of consistency and/or of texture (solid parts, parts that are more or less liquid, semi-solid parts, viscous/viscoelastic parts). This material with a heterogeneous matrix is capable of containing the biological material and/or the biological information sought. By way of example, the sample with a heterogeneous matrix may be a soil, human or animal stool, phlegm or sputum sample, an industrial sample or else a tissue sample (medico-legal samples). Preferably, the sample with a heterogeneous matrix is a human or animal stool sample. According to one particularly preferred embodiment, this sample with a heterogeneous matrix is a human stool sample. The device according to the present invention makes it possible to obtain biological material and/or biological information from all of the types of stools defined by the Bristol scale, namely types 1-7.

For the purposes of the present invention, the term "biological material" is intended to mean any material containing genetic information and which is self-reproducible or reproducible in a biological system. By way of example of the self-reproducible biological material, mention may be made of a microscopic self-reproducible "biological material", such as one or more human, animal or plant cell(s) or one/several bacteria/yeasts.

According to one preferred embodiment of the invention, said biological material is a self-reproducible microbiological material (such as one or more bacterium or bacteria, yeast or yeasts, fungus or fungi) or a biological material (such as one or more viruses) that is reproducible in a biological system. The device according to the present invention is particularly suitable for detecting and/or identifying and/or counting microorganisms that are pathogenic to humans and/or animals.

For the purposes of the present invention, the term "biological information" is intended to mean any element constituting said biological material or produced by the latter, such as nucleic acids (DNA, RNA), proteins, peptides or metabolites. The biological information can in particular be contained within said biological material or excreted/secreted by the latter.

Said "calibrated hollow part", preferably of concave shape, makes it possible to delimit a predetermined volume, suitable for sampling a predefined mass of the material with a heterogeneous matrix. More specifically, the volume of this hollow part is determined so as to contain an amount of biological material and/or of biological information that is sufficient to allow the analysis thereof.

According to one preferred embodiment, the calibrated sampling means comprises a rod and a calibrated hollow part.

According to this preferred embodiment, said calibrated hollow part is connected to the internal part of the stopper by means of said rod.

Advantageously, in order to avoid sampling an excess mass/amount of biological material and/or of biological information, said rod is adapted so that only said at least one calibrated hollow part is capable of containing sample with a heterogeneous matrix. To this effect, said rod is preferably devoid of any recess or cavity, obviously with the exception of said calibrated hollow part. According to one particular embodiment, said rod is made of solid material.

According to one preferred embodiment, said calibrated hollow part is a hollowed-out part of said rod, advantageously located at the level of the end of the rod opposite the internal part of the stopper.

According to one preferred embodiment, said hollow part has at least one wall suitable for removing the surplus sample with a heterogeneous matrix by "scraping" said calibrated hollow part against an appropriate surface, of sufficiently rigid constitution. Thus, by removing the surplus sample with a heterogeneous matrix, protruding outside the volume defined by the calibrated hollow part, the operator is sure that the mass of sample with a heterogeneous matrix removed does not significantly exceed the desired mass, corresponding to the volume of the calibrated hollow part.

Advantageously, said hollow part is calibrated so as to contain a mass of between 10 mg and 2000 mg, preferably between 100 mg and 1000 mg, advantageously between 200 mg and 300 mg, of said material with a heterogeneous matrix.

According to one particular embodiment of the invention, said rod comprises—or is connected to—at least one sliding part, making it possible to pass from a first length of rod to a second length of rod (and, preferably, conversely, namely to pass from said second length of rod to said first length of rod), said second length of rod being less than said first length of rod.

According to a first aspect of this particular embodiment, said rod may be—at least partially—telescopic.

According to a second aspect of this particular embodiment, that is particularly advantageous, the abovementioned sliding part is a sliding extension, suitable for being positioned on said rod and for sliding along the latter in order to pass from said first length of rod to said second length of rod (and, preferably, conversely), said sliding extension comprising at least one calibrated hollow part, preferably positioned at the end of the sliding extension that is furthest from the internal part of the stopper.

According to one particular embodiment of the invention, the sampling means is suitable for containing several calibrated hollow parts, preferably from 2 to 10, preferentially from 2 to 6, advantageously 3 or 6, which can each contain between 10 mg and 2000 mg of said material with a heterogeneous matrix, preferably between 100 mg and 1000 mg, advantageously between 200 mg and 300 mg, of said material with a heterogeneous matrix. Consequently, according to this particular embodiment, the sampling means according to the invention can be suitable for taking an amount of sample with a heterogeneous matrix of between 20 mg and 20 000 mg, preferentially between 200 mg and 6000 mg. Obviously, those skilled in the art will know how to adapt the sampling means according to the invention, in particular with regard to the number and/or the volume of the calibrated hollow part(s), in particular in order to obtain, in fine, a concentration of biological material and/or biological information that is compatible with the minimum level of sensitivity of the analytical techniques. By way of example, it is well known to those skilled in the art that the microorganisms responsible for bovine tuberculosis (mycobacteria of the tuberculosis complex) are difficult to detect and consequently require a larger amount of sample in order to obtain an analyzable concentration of microorganisms.

In one particular embodiment, said sampling means has, on each side of the rod, three calibrated hollow parts that can each contain a volume corresponding to 1000 mg, i.e. a total volume corresponding to 6000 mg, of sample with a heterogeneous matrix, such as bovine, ovine, caprine or porcine feces, advantageously bovine feces.

Typically, the analysis of stools of human origin is carried out using from 200 to 300 mg of sample. However, in certain particular cases, this can range up to 1000 mg. Moreover, in the case of veterinary applications, the mass of sample required for the purposes of the analysis can represent several grams, or even several tens of grams.

According to one preferred embodiment of the invention, the assembly of the stopper and container operates by tight cooperation of the two entities via a closure system, such as a screw-fastening or clip-fastening system, making it possible to close said container such that the content can only leave in the form of filtrate via said at least one opening of said stopper when said container is closed by said stopper.

For the purposes of the present invention, the term "removable closure means" is intended to mean any means which makes it possible to prevent any uncontrolled exit of filtrate. By way of example, said closure means may be a cap or a protective breakable part. In the latter case, said protective breakable part is rigidly connected to said opening, preferably is sealed to the latter (for example by heat sealing) and proves to be breakable, for example by twisting or tensile force. Alternatively, this protective breakable part may be cut via the action of a slicing means, such as a knife or a pair of scissors. It is interesting to note that said breakable part also performs the function of impregnability control, since the fact that this breakable part is separated from the device means, for the operator, that the device in question has already been used. In other words, this breakable part makes it possible to ensure the integrity of the device according to the invention.

Advantageously, when the removable closure means according to the invention is a protective breakable part, the latter has, on the end opposite said opening, a shape complementary to said opening. Thus, when said protective breakable part is separated from said opening, for example by applying a tensile or twisted force to said breakable part, the end of this breakable part having a shape complementary to said opening can be positioned on the latter in order to close it. In this preferred embodiment, said protective breakable part, once separated from the opening, acts as a cap; it thus being possible to describe said protective breakable part as a "protective breakable cap".

As previously indicated, the calibrated sampling means according to the invention is connected to the internal part of the stopper by any appropriate means. Thus, said calibrated sampling means can be screwed, adhesively bonded, assembled by elastic interlocking (for example by clip-fastening) or else forcibly plugged into an opening made in said stopper. According to one particular embodiment, this calibrated sampling means may be heat-sealed to the internal part of the stopper.

According to one preferred embodiment of the invention, said container also comprises at least one mechanical suspending means, which is preferably spherical in shape, such as a bead, suitable for facilitating the suspension of said sample in said suspending solution.

The term "mechanical suspending means" is intended to mean an element suitable for being placed within the container according to the invention and for being moved by one or more force system(s) external to the device according to the invention, for example by manual agitation or agitation induced by the mixing apparatus of the type such as a vortex, sonicator or magnetic stirrer, or bead beater in order to enable/facilitate the mechanical suspending of the sample within said suspending solution.

Advantageously, the device comprises a number of mechanical suspending means, such as beads, selected between 1 and 200, preferably between 5 and 50, advantageously between 10 and 40, particularly preferably between 25 and 35; said mechanical suspending mean(s) having a size of between 1 mm and 10 mm, preferably between 2.5 mm and 3.5 mm, advantageously of approximately 3 mm; preferably, said mechanical suspending mean(s) being made of glass, iron, plastic(s), ceramic(s), particularly preferably of glass.

The size of the mechanical suspending mean(s) is understood to be the largest dimension of the latter. For example, the size of a mechanical suspending means having the shape of a rectangular parallelepiped (straight block) is understood to mean the length (largest dimension) of this rectangular parallelepiped.

As previously indicated, said at least one mechanical suspending means is spherical in shape and advantageously consists of a bead. In the case of a mechanical suspending means that is spherical in shape, the size is understood to be the diameter thereof. Thus, when use is made, as mechanical suspending means, of a plurality of beads having a size of between 2 mm and 10 mm, preferably between 2.5 mm and 3.5 mm, advantageously of approximately 3 mm, it should be understood that the diameter of the beads is between 2 mm and 10 mm, preferably between 2.5 mm and 3.5 mm, said beads advantageously having a diameter of approximately 3 mm. Preferentially, said size of said beads is in agreement with the shape and the dimensions of said calibrated hollow part.

Preferably, the shape and/or the size of said at least one mechanical suspending means is/are suitable so as not to close said at least one opening allowing communication of fluid between the interior of said container and the exterior of said device when said stopper and said container are assembled. Conversely, when the size and/or the shape of said at least one mechanical suspending means is known in advance, the shape and/or the size of said opening can be adapted accordingly, in order to achieve the same objective.

According to one particular embodiment, the mechanical suspending mean(s) has (have) a size (a diameter in the context of mechanical suspending mean(s) of spherical shape) suitable for cooperating with said at least one hollow part of the calibrated sampling means, in particular in order to facilitate the suspending of the sample with a heterogeneous matrix previously taken.

Preferentially, the mechanical suspending mean(s) consist(s) of a material suitable for interacting with an external suspending system/device, said system/device making it possible to move or vibrate the mechanical suspending mean(s) (preferably the beads). Such a system/device may consist, for example, of a sonicator or a magnetic stirrer. Optimally, the material of which the mechanical suspending mean(s) consist(s) interacts little or not at all with said biological material and/or biological information, in particular so as not to modify/degrade said biological material and/or said biological information.

Advantageously, in order to facilitate handling, said calibrated sampling means has sufficient rigidity to prevent said calibrated sampling means from curving while taking sample and to guarantee a low coefficient of variation with respect to the mass of biological matrix sampled.

The term "sufficient rigidity" is intended to mean a rigidity suitable for taking all types of samples with a heterogeneous matrix, and in particular those which have a relatively solid consistency. The sufficient rigidity—and consequently the low elasticity—of the calibrated sampling means makes it possible to facilitate the sampling and to prevent projections of sample with a heterogeneous matrix during the sampling operation.

Advantageously, the sufficient rigidity of the sampling means is obtained by using materials which make it possible to achieve the required degree of rigidity, such as polypropylene (PP), Delrin resin, polyamide (PA) thermoplastic materials, polycarbonate (PC), poly(methyl methacrylate) (PMMA), low-density polyethylene (LDPE), acrylonitrile-butadiene-styrene (ABS) and/or by means of a form which promotes the rigidity of the sampling means. In addition, in order to prevent the calibrated sampling means according to the invention from curving while taking sample, it proves to be important for the connection between said sampling means and the internal part of the stopper to be sufficiently rigid in order to prevent it from folding/curving during the sample-taking operation. Indeed, during this operation, the operator generally holds the external part of the stopper between at least two of his fingers and then takes the desired sample. It is thus important for there to be no weak point at the level of the connection between, on the one hand, the internal part of the stopper and, on the other hand, the calibrated sampling means.

According to one particular embodiment, said calibrated hollow part comprises at least one opening which makes it possible to facilitate the suspending of said sample in said suspending solution.

Preferably, said at least one opening has a circular, ovoid or elongated (preferably oblong) shape. Preferably, said opening is elongated, advantageously oblong, in shape, having for example a stick shape. This elongated, and preferably oblong, shape makes it possible to ensure calibrated and reproducible taking of the sample with a heterogeneous matrix while at the same time promoting the suspending thereof in the suspending solution. According to one particularly preferred embodiment, said at least one opening has a shape and/or a size suitable for cooperating with at least one mechanical suspending means as previously defined, in order to promote the suspending of the sample with a heterogeneous matrix taken by the operator.

According to one particular embodiment, in order to further facilitate this suspending, said at least one hollow part is coated over all or part of its surface (preferably over all of its surface) with a non-stick coating, such as one or more layer(s) of water-soluble material(s) or else a coating of hydrophobic type. Preferably, and in order to facilitate the manufacture of the device, the material chosen for producing the calibrated hollow part has a natural tendency to be hydrophobic and/or exhibits low roughness. By way of example, this low roughness may in particular be obtained by polishing so as to give a polished mirror finish.

According to one preferred embodiment, said container comprises said suspending solution, for example a buffer solution, in a volume sufficient to allow the suspending of the sample.

This suspending can be carried out:
directly, namely by partially or totally, preferably totally, immersing said at least one calibrated hollow part containing the sample in the suspending solution, or
indirectly, by inducing a variation in level of the suspending solution, such that the latter comes into intermittent contact (at regular or irregular intervals) with all or part of said at least one calibrated hollow part containing the sample.

The "indirect" suspending of the sample with a heterogeneous matrix in the suspending solution can in particular occur during a mechanical suspending step, namely, for example, during a stirring/mixing step. The latter can be obtained, for example, by using a stirrer or a mixing apparatus of vortex type.

By way of example of a "suspending solution" it is possible to use any solution suitable for:
i) allowing the suspending of said "sample with a heterogeneous matrix", and/or
ii) preserving the biological matrix and/or the biological information of interest (namely preventing any degradation thereof).

Thus, said suspending solution may be a phosphate buffer (mono/dibasic, 10 mM EDTA, pH 8), a PBS buffer or a TE buffer ("Tris-EDTA"; 10 mM Tris, 10 mM EDTA (Ethylene Diamine Tetraacetic Acid), pH 8). Advantageously, said suspending solution can also comprise a preserving element which preserves the microbial fauna of the sample taken, namely that prevents any modification thereof, in order to allow the sample to be transported at ambient temperature from the site of sampling to the site of analysis, or else to defer the analysis step. A preservative of this type can, for example, consist of a preservative of "Cary-Blair" or "modified Cary-Blair" type, as described in the publication by Srijan et al. [1], or else a trypticase soy broth optionally supplemented with glycerol and/or 5% of sheep blood (in accordance with the teaching of the publication by Wasfy et al. [2]).

Obviously, those skilled in the art will be able to adjust both the nature and the volume of the suspending solution according to the nature and the volume of sample taken.

Advantageously, said suspending solution comprises a calibrator of the plant DNA, plant-derived bacterium or heavy peptides type, etc., making it possible to monitor and control the efficiency of the suspending, filtration and lysis steps (outside the device). In addition, the use of said calibrator is particularly advantageous for validating and interpreting the results. Furthermore, the use of said calibrator directly with the suspending solution makes it possible to dispense with an additional pipetting step in the protocol.

The suspending solution can also comprise a means for capturing non-targeted elements (such as inhibitors, capable of interfering with the subsequent analysis steps). By way of example, active carbon or polyvinyl pyrrolidone (PVPP) can be used as means for capturing non-targeted elements in order to improve the sensitivity of detection, by retaining elements capable of disrupting/inhibiting the subsequent analysis steps.

Moreover, when it is desired to analyze biological information contained in the biological matrix, preferably in the self-reproducible biological matrix, the suspending solution as defined above can, according to one particular embodiment of the invention, also contain a lysis solution, in order to induce the lysis of said biological material and the release of the biological information sought within said sample-suspending solution.

According to one particularly preferred embodiment of the invention, said filtration means is selected from:
- a gradient filter, and
- a superimposition of at least two filters, preferably of two or three filters, the pore size of which decreases from the interior to the exterior of the device.

According to one preferred embodiment, the device is suitable for containing one or more filters each having a surface area greater than 50 $mm^2$, preferably of between 100 and 350 $mm^2$, advantageously between 290 and 330 $mm^2$, in order to limit the clogging of the filters while at the same time ensuring a maximum filtered volume.

The term "gradient filter" (also called "complex filter") is intended to mean a filter which has a plurality of different pore sizes. More specifically, when a gradient filter is used for the purposes of the present invention, the size of the pores of this filter decreases from the interior to the exterior of the device in order to allow gradual and differential filtration of the sample with a heterogeneous matrix of interest.

In any event, whether a gradient filter or a superimposition of at least two filters is used, as previously described, the pore size decreases from the interior to the exterior of the device, preferably from 500 µm to 0.1 µm, advantageously from 200 µm to 10 µm, particularly preferably from 200 µm to 20 µm. Quite obviously, the size of the pores of the filter(s) used is adjusted according to the size of the biological material and/or of the biological information that it is desired to recover in the filtrate.

Thus, when it is desired to isolate, from the sample taken, viruses, toxins, metabolites, or other biological information present within said sample, a pore size of between 0.1 µm and 20 µm, preferentially 0.1 µm and 5 µm, can be used.

In the case of a superimposition of at least two filters, a superimposition of two to four filters is preferably used. Advantageously, a superimposition of two or three filters is used.

In one particular embodiment, said filtration means comprises at least one means for capturing non-targeted elements (such as inhibitors), capable of interfering with the subsequent analysis steps). By way of illustration, said means for capturing non-targeted elements can consist of active carbon, or of a material having a particular affinity for the inhibitors that may be contained in the biological material (proteins, polysaccharides, etc.), for example PVPP.

According to one preferred embodiment, the container comprises at least one wall comprising at least one zone made of flexible material, suitable for undergoing a compression and generating, in response, an overpressure inside said container in order to allow or facilitate the filtration of the content through said filtration means.

Said at least one zone made of flexible material proves to be particularly advantageous, insofar as the operator can generate, on said at least one zone, a manual pressure without excessive force, in order to allow/facilitate the filtration of the content through said filtration means, as previously indicated. The device according to the invention thus allows any laboratory technician, even the least experienced, to obtain, by using the device according to the invention, a filtrate containing the biological material and/or the biological information to be analyzed. Generally, the device according to the invention can fit to any system/device which makes it possible to facilitate the filtration operation. For example, said device can be fitted to a vacuum filtration system or to a centrifugation filtration system. It results from the aforementioned that the device according to the invention can, contrary to the protocol for obtaining biological material and/or biological information of the prior art, be easily automated, for example by means of an automated filtration device (or automatic filtration device), which is also a subject of the present invention. Such an automated filtration device, suitable for allowing the automation of the step of filtration of the content (namely of the suspension containing the sample with the heterogeneous matrix of interest), comprises:
- at least one site (and preferably a plurality of sites) suitable for receiving and maintaining the device for obtaining biological material and/or biological information according to the invention, preferably in the "inverted" or "upside down" position (namely in which the abovementioned opening essentially points downward),
- a pressure member (for example a press such as a piston), which is mobile from an initial position ("resting position") to a "pressure" position, in which said pressure member is suitable for exerting a pressure against said at least one zone made of flexible material, thereby having the effect of generating, in response, an overpressure inside said container, and thus allows the filtration of the content through said filtration means to a collecting receptacle (for example a tube, such as an Eppendorf® tube).

Optimally, the automated filtration device according to the invention comprises up to eight or even ten different sites, thereby making it possible to simultaneously filter up to eight or even ten devices for obtaining biological material and/or biological information according to the invention.

Preferably, the pressure member is actuated by a motor on command from the user or from an automated control center. For example, the user starts the motor by activating a switch (for example by pressing on a push-button), which has the effect of causing the pressure member to go from an initial position ("resting position") to a "pressure" position, in which said pressure member exerts a pressure against said at least one zone made of flexible material.

According to one particularly advantageous embodiment of the invention, the abovementioned automated filtration device is provided with an optical level detector (also called "optical barrier") which stops the filtration step when the desired level of filtrate is reached within the collecting receptacle. More specifically, this optical detector operates by causing the pressure member to go from the pressure position to the resting position (under the action of the motor or, more simply, by stopping said motor), namely stops the pressure exerted by the pressure member on the zone made of flexible material when the optical level detector detects, via an optical sensor, that the desired level of filtrate is reached within the collecting receptacle, thus ending the filtration step. Without being bound by any theory, the fact that the pressure member ceases to exert a pressure against said at least one zone made of flexible material has the effect of ending the overpressure previously generated inside the container, which causes the filtration step to be stopped when the desired level of filtrate is reached within the collecting receptacle. An automated filtration device according to the invention, provided with an optical level detector, proves to be particularly advantageous, insofar as it makes it possible to collect the same volume of filtrate, this being whatever the type of stools, ensuring that the process for obtaining biological material and/or biological information using the device for obtaining biological material and/or biological information according to the invention is repeatable and robust. This is especially true given that, as previously explained, the calibrated hollow part of the device for obtaining biological material and/or biological information according to the invention makes it possible to take a given/predefined mass of sample with a heterogeneous matrix (without having to perform weighing operations), said mass being constant or virtually constant at each operation of taking a sample with a heterogeneous matrix. In other words, said calibrated hollow part and the automated filtration device according to the invention, provided with an optical level detector, act in synergy in order to guarantee optimal repeatability and robustness of the process for obtaining biological material and/or biological information using the device for obtaining biological material and/or biological information according to the invention.

In one preferred embodiment, said stopper comprises at least one rigid zone, said rigid zone having a shape suitable for cooperating with at least one maintaining member, such as a clip, connected to a mixing apparatus, such as a vortex, so as to allow said device to be maintained on the mixing apparatus during the mixing of said device in order to facilitate the suspending of said sample in said suspending solution.

According to one preferred embodiment, said rigid zone has a shape suitable for cooperating with a clip connected to said mixing apparatus, said rigid zone comprising:
  at least one anti-rotation means, comprising two distinct bearing surfaces, for example made up of two shoulders or of two tabs, each of the two distinct bearing surfaces being suitable for butting against or coming into abutment against one of the two ends of the clip when the stopper undergoes a rotational movement, in order to prevent or stop said rotation, and/or
  at least one anti-translation means, comprising at least one bearing surface, such as a lip, a collar or a shoulder, said at least one bearing surface being suitable for butting against or coming into abutment against said clip when the stopper undergoes a translational movement, in order to prevent or stop said translational movement.

Said at least one rigid zone allows the device of the invention to easily fit to the commercially available mixing/homogenizing apparatuses, such as apparatuses of vortex type, and to obtain results that are at the very least equivalent to those observed with devices specifically designed for this purpose, of the bead beater type.

The abovementioned anti-rotation means and/or anti-translation means make(s) it possible to improve the maintaining of the device according to the invention by the maintaining member (for example a clip of the mixing apparatus of vortex type).

The anti-rotation means makes it possible to limit, and preferably to eliminate, any rotation of said stopper (and thus, by extension, of the device according to the invention) relative to the abovementioned maintaining member. In addition to the fact that the anti-rotation means makes it possible to ensure entirely satisfactory maintaining between the stopper—and thus the device according to the invention—and the maintaining member of the mixing apparatus, this anti-rotation means also has the function of orienting the stopper, and consequently the calibrated sampling means, which is rigidly connected to said stopper, such that the calibrated hollow part of said sampling means is oriented downward or upward, preferably downward, when the device according to the invention is positioned on the maintaining member of the mixing apparatus.

Regarding said anti-translation means, it makes it possible to limit, and preferably to eliminate, any translational movement of the stopper (and thus, by extension, of the device according to the invention) according to a vector that is oriented in the stopper-containing direction during the mixing operation. This anti-translation means thus makes it possible to ensure efficient mixing and to prevent the device according to the invention from getting away from the maintaining member during said mixing operation. Advantageously, this anti-translation means comprises at least one lip (protruding part) positioned on all or part of the surround of the upper part of the stopper.

According to one particular embodiment, this anti-translation means consists of a collar (circular part) positioned on the upper part of the stopper and connected to the latter, having a diameter greater than the diameter of the body of the stopper.

The lip formed on all or part of the surround of the upper part of the stopper constitutes a bearing face, which will cooperate with the abovementioned maintaining member (such as a clip) in order to guarantee the maintaining of the stopper—and thus of the device according to the invention—during the mixing operation. According to one preferred embodiment, when the maintaining member is a clip, the bearing face made up of the lip or the collar, as mentioned above, will come into abutment against said clip in order to prevent or stop any translational movement as explained hereinafter, under the title "detailed description of the invention".

According to one preferred embodiment of the invention, the upper part of the container—advantageously the shoulder of the flask should said container be a flask—performs the function of anti-translation means while making it possible to limit, or even eliminate, any translational movement of the stopper (and thus, by extension, of the device according to the invention) according to a vector that is oriented in the container-stopper direction during the mixing operation. Indeed, the bearing face made up of the upper part of said container (for example the shoulder of the flask) butts against/comes into abutment against said maintaining member in order to prevent or stop any translational movement of the device according to the invention according to a vector that is oriented in the container-stopper direction.

According to one variant of the invention, a second anti-translation means can be positioned on all or part of the surround of the lower part of the stopper, in order to limit, or even eliminate, any translational movement of the stopper (and thus, by extension, of the device according to the invention) according to a vector that is oriented in the container-stopper direction during the mixing operation.

Generally, said device is a device for obtaining biological material, preferably microbiological material, and said filtration means is suitable for allowing the selective passage of said biological material, preferably of said microbiological material, to the exterior of said device.

A subject of the invention is also the stopper per se as previously defined.

In addition, the invention also relates to the use of the abovementioned device for obtaining biological material and/or biological information from a sample with a heterogeneous matrix, preferably for obtaining biological material, preferably for obtaining microscopic biological material, advantageously for obtaining microbiological material. Said filtration means is suitable accordingly, in order to allow the selective passage of said biological material, preferably of said microscopic biological material, advantageously of said microbiological material, to the exterior of said device.

According to one preferred embodiment, and as previously indicated, the sample with a heterogeneous matrix is selected from a soil sample, a stool sample, a sample of necrosed tissue, a food sample and an industrial sample, said sample preferably being a human or animal stool sample.

Advantageously, said sample with a heterogeneous matrix is a stool sample.

Another subject of the invention relates to a process for obtaining biological material and/or biological information from a sample with a heterogeneous matrix, said process using the device according to said process comprising the following steps:
- a) taking a predetermined volume of sample corresponding to a given mass using said calibrated sampling means,
- b) suspending said sample in said suspending solution, optionally by mechanical suspending,
- c) filtering the suspension obtained in step b) through said filtration means in order to obtain a filtrate containing said biological material and/or said biological information.

According to one particular embodiment, the operator may store the suspension obtained following the abovementioned step b) and, where appropriate, defer the filtration step c). This makes it possible in particular to preserve the biological material and/or the biological information of interest for the purposes of subsequent analysis or analyses or, in the case of samples taken "in the field" (namely outside the laboratory), to send, to a laboratory, the device according to the invention comprising the suspension obtained in step b), namely comprising the biological material and/or the biological information of interest, obtained from the taking of a sample with a heterogeneous matrix. This in fact proves to be particularly advantageous when the samples with a heterogeneous matrix are taken in remote areas (in areas of the bush, for example), that are a long way from any analytical laboratory. In this embodiment, at least one preserving means suitable for the nature of the biological material and/or of the biological information to be analyzed is preferably used. Thus, said suspending solution may, for example, contain one or more chemical preservative(s) (for example of the Cary-Blair type) and/or one or more freezing mean(s) (allowing, by way of illustration, freezing at a temperature of about −80° C.). Quite obviously, the indispensable condition is that the preserving mean(s) used does (do) not (or, where appropriate, not significantly) modify the biological material and/or the biological information to be analyzed.

According to one particular embodiment, said suspending solution comprises at least one culture means. This culture means may be at least one nutritive element or a plurality of nutritive elements (for example a culture medium) making it possible to promote the growth of all of the microorganisms present in the sample taken or to more or less selectively direct the growth of one or more type(s) of microorganisms.

Said at least one culture means may also be at least one selective agent having inhibitory properties with regard to the growth of at least one type of microorganism, such as an antibiotic (bactericidal or bacteriostatic, preferably bactericidal) or an antifungal. The use of at least one selective agent can make it possible to direct the growth of at least one type of microorganism.

Quite obviously, those skilled in the art will adjust the culture mean(s) present in the suspending solution according to the type(s) of microorganisms of interest.

Another subject of the invention relates to a process for extracting biological information (for example nucleic acids, such as DNA and/or RNA) from a sample with a heterogeneous matrix, said process comprising the following steps:
- a) carrying out the abovementioned process for obtaining biological material and/or information in order to obtain a filtrate containing said biological material and/or said biological information,
- b) when the biological information that must be extracted is contained within said biological material, such as a cell, a bacterium, a fungus or a yeast, carrying out a step of lysis of said biological material, preferably a step of mechanical lysis, in order to obtain a lysate comprising the biological information that must be extracted,
- c) extracting the biological information from the filtrate obtained in step a) or from the lysate obtained in step b) by carrying out a suitable process for extracting biological information.

According to one preferred embodiment, this extraction process is a process for extracting nucleic acid(s) (genetic information). In this embodiment, the abovementioned lysis step b) of the extraction process can be integrated into the extraction step c). For example, some automated systems for extracting genetic information of easyMAG® type (bioMérieux) integrate a lysis step into the extraction protocol. Said lysis may in particular be of chemical, mechanical or thermal type, depending on the nature of the sample with a heterogeneous matrix, on the biological material and/or biological information sought or else on the analytical techniques that will be subsequently used.

According to one preferred embodiment, said process for extracting biological information comprises, before step c), and before step b) when said step must be carried out, a step of concentrating said biological material and/or said biological information, preferably by centrifugation (with or without density cushion of cesium chloride type for example) or by flocculation. When said concentrating step is carried out by centrifugation, the latter is carried out at a speed of between 6000 g and 12 000 g, advantageously of approximately 12 000 g.

Another subject of the invention relates to a process for analyzing biological information, said process comprising the following steps:
- a) extracting said biological information to be analyzed using the abovementioned process for extracting biological information,
- b) identifying and/or quantifying said biological information by any appropriate method of analysis, for example a method of genetic analysis such as a PCR, or a method of immunoassay or enzymatic assay type.

According to one preferred embodiment, this analysis process is a process of genetic analysis (analysis of nucleic acid(s)). In this situation, said biological information is genetic information and the identification and/or quantification of this genetic information is (are) carried out by any appropriate method of genetic analysis, for example by PCR.

In addition, a purification step may, as required, be carried out before step d), in order to remove any non-targeted element (such as one or more inhibitor(s) capable of interfering with the method(s) of analysis used in step d)).

Another subject of the invention relates to a process for analyzing biological material from a sample with a heterogeneous matrix, said process comprising the following steps:

a) obtaining a filtrate containing the biological material to be analyzed by using the abovementioned process for obtaining biological material,
b) where appropriate, inoculating a reaction medium with the filtrate obtained in step a), said reaction medium being suitable for allowing the growth and/or the expression of at least one metabolism of said biological material,
c) where appropriate, incubating the filtrate obtained in step a), or the inoculated reaction medium obtained in step b), for an appropriate period of time and at an appropriate temperature,
d) analyzing the biological material resulting from step a), b) or c) by any appropriate means of biological analysis.

According to one preferred embodiment, said biological material is a microbiological material.

In one particular embodiment, step a) of the process for analyzing biological material can be suitable for the analysis of "fragile" biological materials, such as Gram-bacteria, in particular using suspending means which cause fewer mechanical stresses on the bacteria walls. In order to allow suspending that is less damaging to these bacteria, the operator can reduce the mixing frequency, using mechanical suspending means which have a greater size, or else eliminate the use of mechanical suspending means. In the case where a mechanical suspending means would not be used, or where the sample would be difficult to suspend, a calibrated hollow part having at least one opening—preferably a plurality of openings—can be used in order to facilitate the suspending. Obviously, those skilled in the art will be able to adjust these parameters according to the biological material of interest termed "sensitive" and to the nature of the sample.

Preferentially, the abovementioned process for analyzing microbiological material comprises step b) and optionally step c), advantageously steps b) and c), in which:
  step c), when it is present, consists in incubating the inoculated reaction medium obtained in step b) for an appropriate period of time and at an appropriate temperature, and
  step d) of analyzing biological material consists of the detection and/or identification and/or counting of said biological material on/in said reaction medium, preferably by visual or optical reading.

Another subject of the invention relates to a kit for obtaining biological material and/or biological information from a sample with a heterogeneous matrix, said kit comprising:
  said container and said stopper, in assembled or disassembled form,
  at least one suspending solution, suitable for allowing said sample to be suspended,
  preferably at least one mechanical suspending means, such as at least one bead.

Advantageously, said container and said stopper are in disassembled form and are preferably packaged sterily.

Another subject of the invention relates to the use of the abovementioned kit for carrying out said process for obtaining biological material and/or biological information.

According to one preferred mode of the present invention, the device according to the invention is suitable for taking a sample of fecal material for the purposes of the microbiological analysis thereof.

The biological material and/or biological information present in the filtrate obtained using the device according to the invention can be analyzed by various methods of biological analysis, such as enzymatic or immunological assays, nucleic sequence amplifications or tests on a Petri dish, or else by sequencing. In addition, the biological material and/or biological information present in the abovementioned filtrate can, where appropriate, be concentrated, purified, lysed or cultured, or enriched or be directly analyzed.

By way of example, the biological material and/or biological information present in the abovementioned filtrate can be directly analyzed by MALDI-TOF mass spectrometry (depositing of at least one drop of filtrate on a MALDI-TOF plate), by Raman spectroscopy, by immunochromatography on a membrane or strip (lateral flow test), or by systems of bacteria identification of the API strip type.

BRIEF DESCRIPTION OF THE DRAWINGS

The invention, its functionality, its applications and also its advantages will be more clearly understood on reading the present description, given with reference to the figures, in which:

FIG. 14 represents a perspective view of a second embodiment of the calibrated sampling means according to the invention, FIG. 15 shows a perspective view of a third embodiment of the calibrated sampling means according to the invention, FIG. 16 is a perspective view of a stopper comprising a fourth embodiment of the calibrated sampling means according to the invention.

DETAILED DESCRIPTION OF THE INVENTION

The objective of the detailed description hereinafter is to set out the invention sufficiently clearly and completely, in particular with reference to the abovementioned figures, but should not in any way be regarded as limiting the scope of the protection to the particular embodiments which are the subject of said figures.

Figure 1:
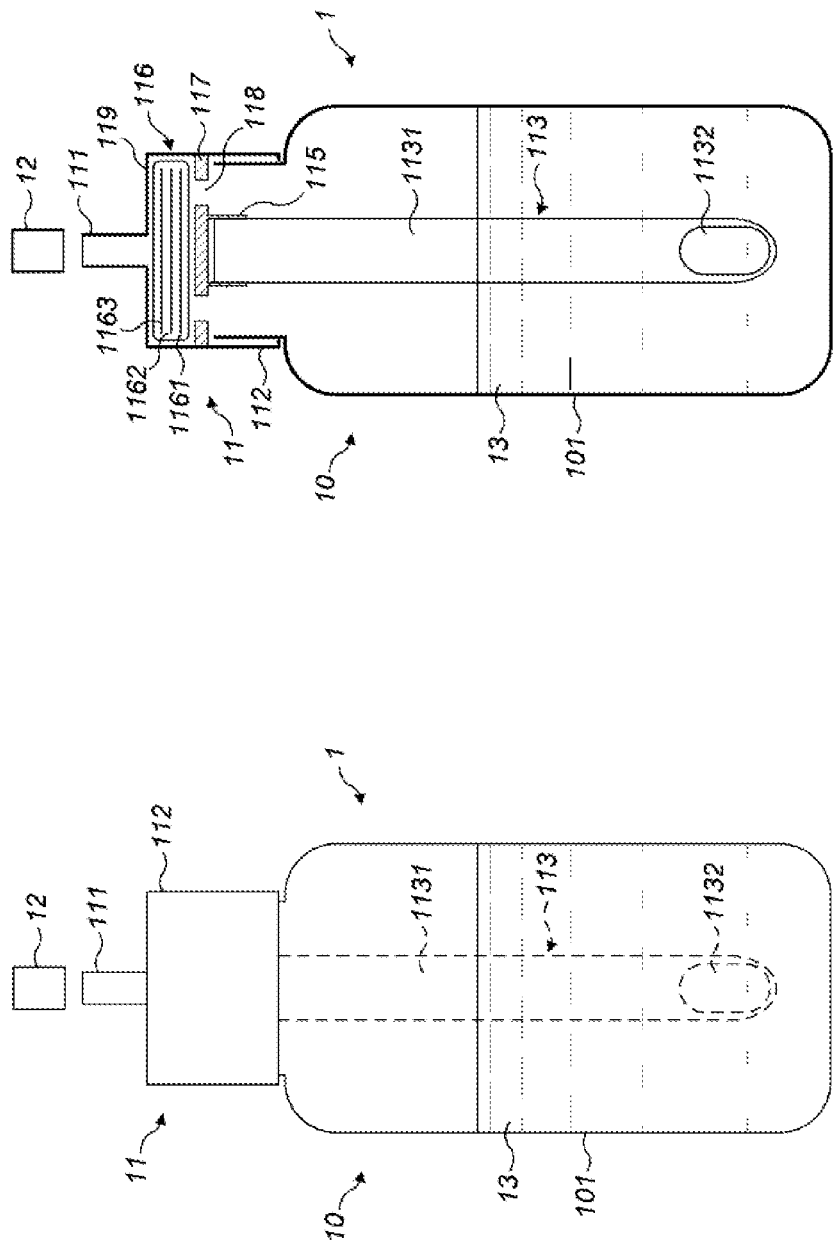
FIGS. 1A and 1B show, respectively, a face-on view and a sectional view of a first embodiment of the device according to the present invention.

As represented in FIG. 1A, the device according to the invention comprises a container 10, which is in the form of a flexible plastic flask, that can be deformed in particular via a pressure exerted on said container by the operator's fingers.

The flexible wall 101 of the abovementioned container 10 is made of flexible material. This flexible wall 101 contains, for example, rigid paper, cardboard, polyethylene, polyvinyl chloride, polypropylene, low-density polyethylene, polyethylene terephthalate, and also any suitable combination of these materials and/or of any other biobased material so that the flexible wall 101 of the container 10 has satisfactory properties in particular in terms of rigidity (in order to be able to place the container on a flat surface), of leaktightness and of deformation by compression when a pressure is exerted (for example by the operator's fingers or by the pressure member of an automated filtration device, as described above or below) on the flexible wall 101 of the container 10, during the filtration step.

As represented in this FIG. 1A, the container 10 is closed by means of a stopper 11 comprising, from its upper part to its lower part:
  a tubular-shaped orifice 111, making it possible in fine to harvest the filtrate (that can be closed by a cap 12),
  a stopper body 112 (central part),
  a calibrated sampling means 113 connected to the lower part of the stopper 11 (not numbered in FIG. 1A).

More specifically, this calibrated sampling means 113 comprises a calibrated hollow part 1132 connected to the lower part of the stopper (not numbered on FIG. 1A) by means of a rod 1131. The volume of the calibrated hollow part 1132 has been calculated beforehand to correspond to a predetermined mass of sample with a heterogeneous matrix, capable of containing the biological material and/or the biological information of interest.

The device 1 is formed by assembly of the stopper 11 and of the container 10.

The container 10 is filled with a sufficient volume of suspending solution 13, as previously defined. The level of suspending solution 13 is represented in FIGS. 1A and 1B purely by way of indication.

The internal structure of the stopper 11—and in particular of the stopper body 112—is clearly visible in FIG. 1B, which represents a sectional view of the device 1. The stopper body 112 comprises an internal part 117 and an external part 119, these two parts 117 and 119 delimiting a cavity within which a filtration means 116 is placed. This filtration means 116 consists of a superimposition of three filters 1161, 1162 and 1163, each having a surface area of 314 $mm^2$; each of the three filters 1161, 1162 and 1163 also having pores of degressive sizes from the internal part 117 to the external part 119 of the stopper body 112. More specifically, the first filter 1161 has pores of which the size is between 100 µm and 200 µm, whereas the two "upper" filters 1162 and 1163 each have pores of less than 50 µm in size. The first filter 1161 makes it possible to remove the coarsest entities (for example cell debris, etc.), whereas the two "upper" filters 1162 and 1163 make it possible to provide the selectivity of the filtration operation. As illustrated in FIG. 1B, the filter 1163 having the smallest pore sizes (equal to those of the filter 1162) comes into contact with the external part 119 of the stopper body 112.

The rod 1131 of the calibrated sampling means 113 is connected to the internal part 117 of the stopper 11 by a connecting (or fixing) means 115, placed on said internal part 117.

Openings 118 are made within the part 117 of the stopper 11 in order to allow the passage of the suspending solution 13 comprising the sample with a heterogeneous matrix (not represented) to the tubular-shaped orifice 111 via the filtration means 116, comprising the superimposition of the three filters 1161, 1162 and 1163.

For the purposes of clarity, the use of the device 1 according to the invention is briefly described hereinafter.

Using the hollow part 1132 of the calibrated sampling means 113, the user samples a volume corresponding to the volume defined by the calibrated hollow part 1132 and corresponding to a desired mass of sample with a heterogeneous matrix. The container 10 with a flexible wall 101 is filled with a sufficient volume of a suspending solution 13. As illustrated in FIGS. 1A and 1B, the container 10 is closed/blocked by the stopper 11 (for example the stopper 11 is screwed onto a thread placed on the neck of said container) and, optimally, the tubular-shaped orifice 111 is closed by the cap 12.

The device 1 is then stirred in order to allow the suspending of the sample with a heterogeneous matrix contained in the calibrated hollow part 1132 of the sampling means 113. Once the suspending has been carried out, the operator removes, as appropriate, the cap 12 and "turns" the device 1 "upside-down" (said device 1 thus being in an "inverted" or "upside-down" position, namely in which the tubular-shaped orifice 111 points essentially downward). Owing to this turning upside-down operation, the suspending solution 13, loaded with sample with a heterogeneous matrix, passes through the openings 118 made within the internal part 117 of the stopper 11, passes successively through the three filters 1161, 1162 and 1163 of the filtration means and flows to the exterior, in the form of a filtrate, by the tubular-shaped orifice 111. The filtrate is then collected in any type of appropriate receptacle, for example in an Eppendorf tube.

Advantageously, and as previously indicated, the passing of the suspending solution 13, loaded with sample with a heterogeneous matrix, through the filtration means 116 is facilitated/accelerated when the operator exerts a pressure on the flexible wall 101 of the container 10, resulting in an overpressure within said container 10 and in particular at the level of the filtration means 116. This operation of compression of the flexible wall 101 by the operator proves to be particularly advantageous for facilitating the filtration, given the smallness/narrowness of the pores of the two upper filters 1162 and 1163.

Figure 2:
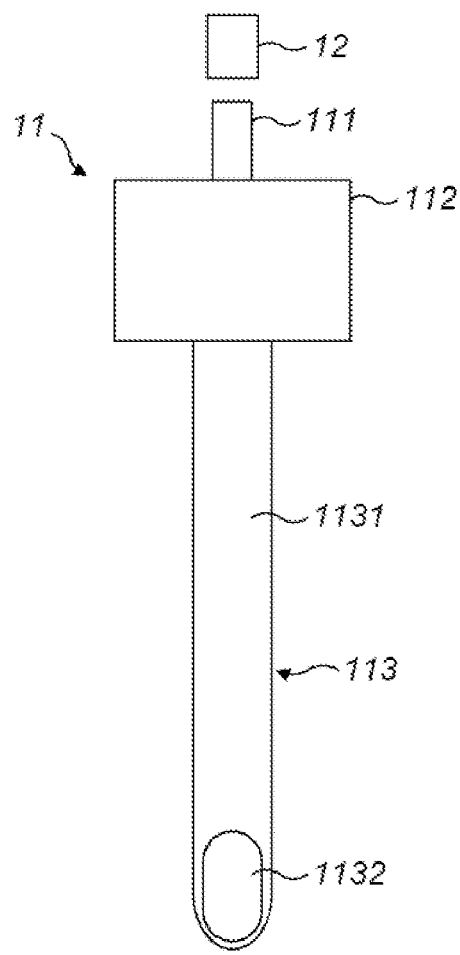
FIG. 2 represents a face-on view of the stopper, separated from the container as represented in FIGS. 1A and 1B.

The view represented in FIG. 2 makes it possible to visualize the stopper 11, when said stopper is disassembled from the container 10, for example by unscrewing said stopper 11. In this FIG. 2, the tubular-shaped orifice 111, which can be closed by means of the cap 12, the stopper body 112 and the calibrated sampling means 113 are distinctly observed. As represented in FIGS. 1A and 1B, the latter comprises a rod 1131 connected, via one of its ends, to the internal part of the stopper body 112 and comprising, at the level of its opposite end, a calibrated hollow part 1132.

Figure 3:
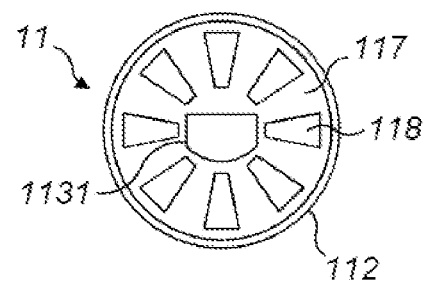
FIG. 3 is a view from below of the stopper of FIG. 2.

As previously indicated, FIG. 3 is a view from below of the stopper 11. Clearly seen in this FIG. 3 is the radial arrangement of the openings 118, made within the internal part 117 of the stopper 11, around the rod 1131 of the sampling means 113. Although the number and arrangement of the openings 118 can vary as desired by those skilled in the art, the radial arrangement of the openings 118 as represented in FIG. 3 allows a good distribution of the volume of the suspending solution 13 loaded with sample with a heterogeneous matrix to the filtration means (not represented in FIG. 3) via said openings 118.

Figure 4:
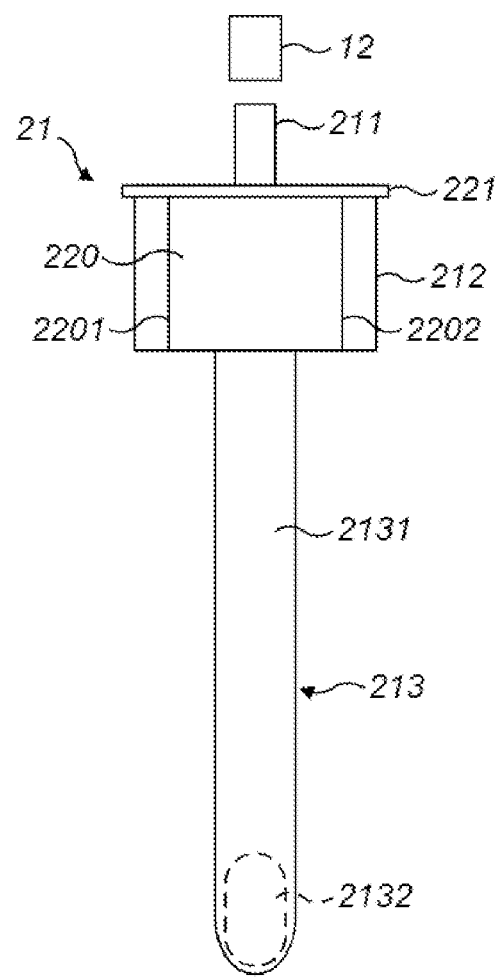
FIG. 4 is a face-on view of a stopper according to a second embodiment, separated from the container according to the invention.

FIG. 4 illustrates a second embodiment of a stopper 21 according to the invention. The stopper body 212 is provided:
with an anti-rotation means 220, and
with an anti-translation means 221, both suitable for cooperating with a maintaining member such as a clip (not represented), of a mixing apparatus, such as a vortex (also not represented in FIG. 4).

The anti-rotation means 220 is positioned on the exterior surface of the stopper body 21. As represented in FIG. 4, the anti-rotation means 220 is formed by an overthickness at the surface of the body of the stopper 21. This overthickness defines two shoulders 2201 and 2202 on the stopper body 212.

When the maintaining member of the mixing apparatus (not represented in FIG. 4) is a clip, each of the two branches of this clip will come to position itself on either side of the anti-rotation means 220. When the stopper 21 is given impetus to rotate during the mixing step, one of the two shoulders 2201 or 2202 (depending on the direction of rotation) will come into abutment on the end of one of the two branches of the clip, preventing or stopping, de facto, the rotation of said stopper 21. Preferably, the stopper is positioned on the clip such that the shoulders 2201 and 2202 come into abutment against the ends of each of the two branches of the clip.

This anti-rotation means proves to be particularly advantageous insofar at it makes it possible to impose a particular orientation on the calibrated sampling means 213 connected to the internal part (not represented in FIG. 4) of the stopper 21. Thus, the anti-rotation element 220 is positioned on the external surface of the stopper body 212 in such a way that the calibrated hollow part 2132 of the sampling means 213 is oriented downward when the device comprising the stopper 21 is placed on the maintaining member (for example a clip) of the mixing apparatus of vortex type. This "downward" orientation of the hollow part makes it possible to improve the suspending of the sample with a heterogeneous matrix that it contains.

The anti-translation means 221, as represented in FIG. 4, is formed by a collar with a diameter greater than that of the stopper body 212. The function of this anti-translation means 221 will be described hereinafter, in relation to FIG. 5.

The arrangement of the anti-rotation means 220 and the anti-translation means 221 relative to the stopper body 212, and in particular to the internal part 217 of this stopper body 212, is clearly illustrated in FIG. 5, which represents a view from below of the stopper 21 according to the second embodiment of the invention, said stopper 21 being disassembled from the container 10. As is the case in FIG. 3, the radial arrangement of the openings 218 around the rod 2131 of the sampling means 213 is here again observed.

Figure 6:
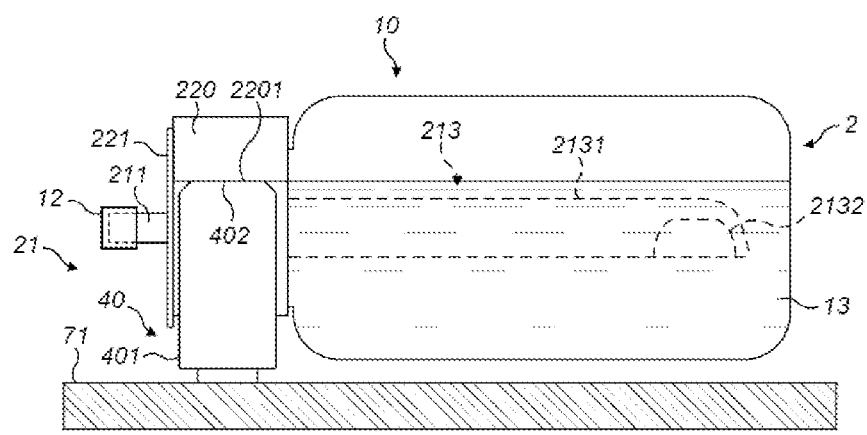
FIG. 6 represents a side view of a device according to the invention connected to a mixing apparatus by means of a clip.

FIG. 6 makes it possible to visualize the maintaining of the device 2 (comprising the stopper 21 according to a second embodiment and the container 10) on a mixing apparatus 71 via the cooperation of the stopper body 212 and of a clip 40, connected to the mixing apparatus 71. In this regard, it should be noted that the clip 40 can be an integral part of the mixing apparatus 71 or can be connected thereto by any appropriate means. More specifically, it is observed, in this figure, that the shoulder 2201 of the anti-rotation means 220 comes into abutment against the end 402 of the corresponding branch of the clip 40. Quite obviously, the shoulder 2202 also comes into abutment against the end 403 of the corresponding branch of the clip 40, even though this cannot be observed in FIG. 6. In other words, the anti-rotation means 220 "butts" against each of the two ends 402 and 403 of the clip 40, such that the stopper 21, and consequently the device 2, cannot undergo any rotational movement, in one direction or the other. Entirely advantageously, it is noted, in this FIG. 6, that the anti-rotation means 220 has been positioned on the external surface of the stopper body 212 so as to orient the calibrated hollow part 2132 "downward" when the stopper 21 is maintained by the clip 40. As previously indicated, the orientation of the calibrated hollow part 2132 downward makes it possible to ensure optimal suspending of the sample with a heterogeneous matrix.

In addition, the anti-translation means 221 is also clearly visible in FIG. 6. As previously indicated, it is, in this embodiment, a collar with a diameter greater than that of the stopper body 212. When a translational movement occurs according to a vector that is oriented in the stopper 21—container 10 direction, the collar acts as a bearing face, which comes into abutment against the part 401 of the clip 40, thus preventing or stopping this translational movement.

As represented in FIG. 6, the container 10 is filled with a sufficient volume of suspending solution 13, as previously defined. The level of this suspending solution 13 is represented purely by way of indication in FIG. 6. The tubular-shaped orifice 221 of the stopper 21 is also closed by the cap 12, in order to prevent any untimely exit of the suspending solution 13 during the mixing step.

Figure 7:
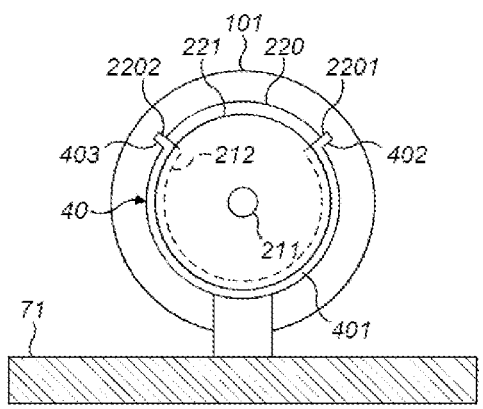
FIG. 7 is a face-on view of the device according to the invention-clip-mixing apparatus assembly as represented in FIG. 6, FIGS. 8A and 8B are perspective views of a stopper according to a third embodiment.

FIG. 7 represents a face-on view of the stopper 21, maintained by the clip 40, itself connected to the mixing apparatus 71. In this FIG. 7, the positioning of the clip 40 on either side of the anti-rotation means 220, such that each of the two shoulders 2201 and 2202 come into abutment against the corresponding ends 402 and 403 of each of the two branches of the clip 40, is clearly distinguished.

This clip 40 is also positioned under the anti-translation means 221. In the event of there being a translational movement (according to a vector that is oriented in the stopper 21—container 10 direction), the collar constituting the anti-translation means 221 will come into abutment against the part 401 (not represented in FIG. 7) of the clip 40 so as to prevent or stop any translational movement.

Figure 8A:
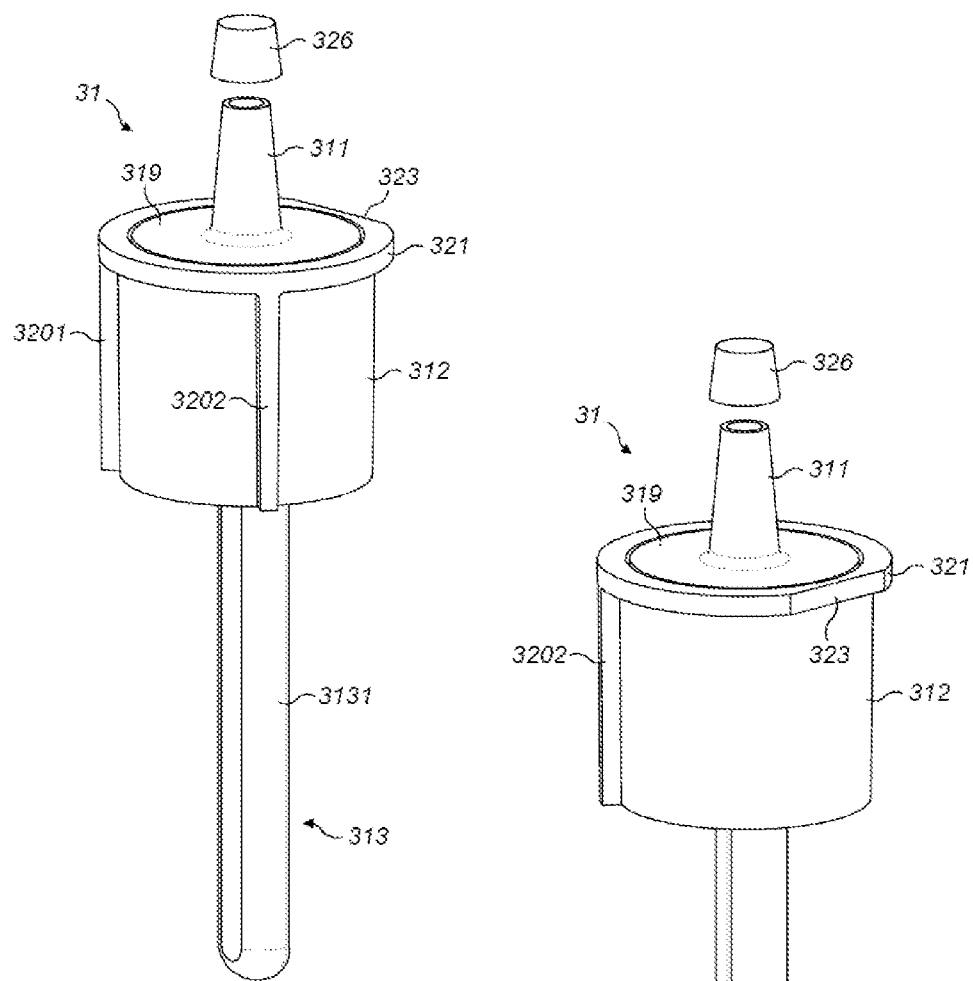
Figure 8B:
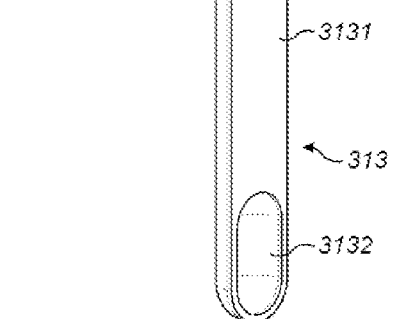

A third embodiment of the stopper 31 is illustrated in FIGS. 8A and 8B. The latter clearly represents this stopper 31, which comprises, from the upper part to the lower part:
- a tubular-shaped orifice 311,
- an upper part 319,
- an anti-translation means 321,
- a stopper body 312,
- an anti-rotation means 3201, 3202,
- a calibrated sampling means 313 comprising a rod 3131 and a hollow part 3132.

In addition, the tubular-shaped orifice 311 can be closed by means of the cap 326.

As is possible to note in the light of FIGS. 8A and 8B, this hollow part 3132 is oriented in a manner opposite to the anti-rotation means 3201, 3202. In this way, when the device comprising the stopper 31 and the container 10 is maintained by a clip connected to a mixing apparatus, the anti-rotation means 3201, 3202 is oriented upward, as illustrated in FIG. 6, whereas said calibrated hollow part 3132 is deliberately oriented downward, in order to promote the suspending of the sample with a heterogeneous matrix present in the calibrated hollow part 3132.

In addition, contrary to the stopper according to a second embodiment of the invention, represented in FIGS. 4-7, in which the anti-rotation means 3201, 3202 is formed by an overthickness of material (for example an overthickness of plastic), positioned on the width of a part of the stopper body 212, the anti-translation means 3201, 3202 of the stopper 31 comprises, over the entire length of the stopper body 312, two parallel tabs 3201, 3202, present at the surface of the stopper body 312.

Figure 5:
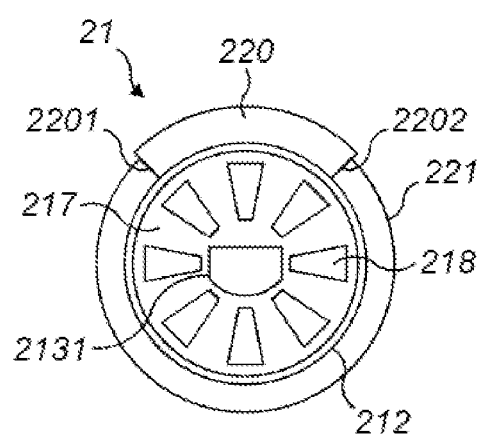
FIG. 5 represents a view from below of the stopper represented in FIG. 4.

As for the shoulders 2201 and 2202 represented in FIG. 5, when the stopper 21 is given impetus to rotate during the mixing step, one of the two tabs 3201, 3202 (depending on the direction of rotation) comes into abutment on the end of one of the two branches of the clip, preventing or stopping, de facto, the rotation of said stopper 31.

Preferably, the stopper 31 is positioned on the clip such that the tabs 3201, 3202 come into abutment against the ends of each of the two branches of the clip.

The various parts constituting the stopper 31, previously presented with reference to FIGS. 8A and 8B, with the exception of the calibrated sampling means, are described hereinafter.

Figure 9:
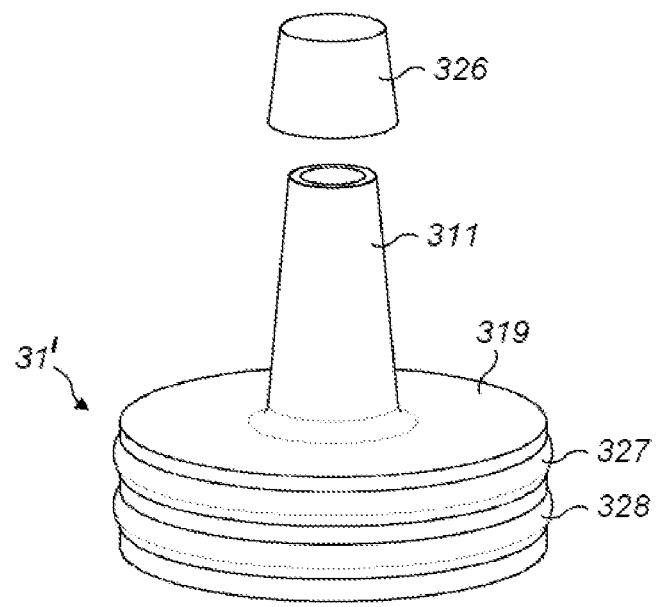
FIG. 9 shows a face-on view of the pouring spout of the stopper represented in FIGS. 8A and 8B.

The pouring spout 31' of this stopper 31 is represented in FIG. 9. In said figure, a removable cap 326 having a shape complementary to that of the tubular-shaped orifice 311, is observed, from the upper part to the lower part. This cap 326 can in particular be of cylindrical shape or of truncated conical shape.

The pouring spout 31' also comprises the upper part of the stopper body 319 and two rings, 327 and 328, placed parallel to one another about the upper part of the stopper 319. The assembly formed by the two rings 327 and 328 represents a male elastic interlocking element (commonly denoted "male clip-fastening element") suitable for cooperating with a female elastic interlocking element (commonly denoted "female clip-fastening element"). The latter is obtained by reaming of the central element 31", represented in FIG. 10 and described hereinafter.

FIGS. 8A and 8B also represent a means for consistent positioning in a flattened area 323 of the anti-translation means 321, making it possible to position the stopper relative to the ends 402 and 403 of each of the two branches of the clip 40 and to thus prevent the anti-translation means 321 from coming into contact with the mixing apparatus 71.

Figure 10:
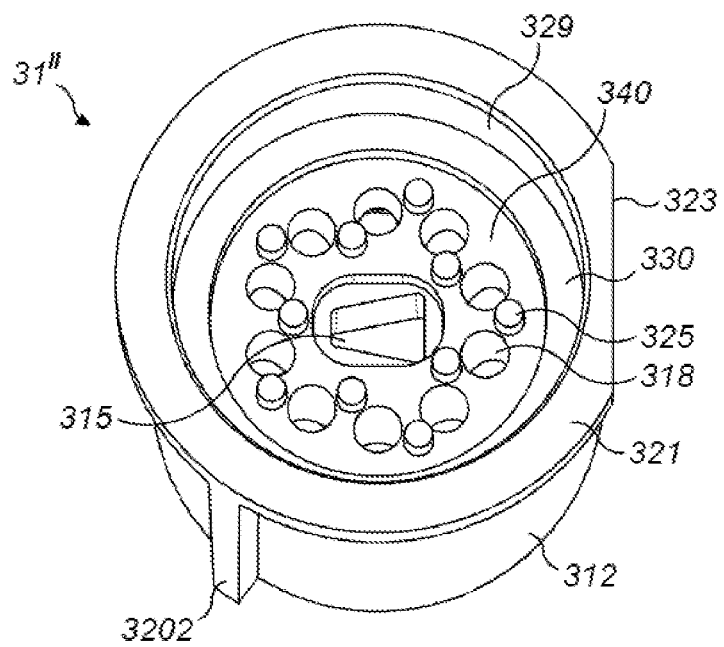
FIG. 10 is a perspective view of the upper plane of the central part of the stopper represented in FIGS. 8A and 8B.

FIG. 10 makes it possible to precisely observe the upper part of the central element 31", comprising various filter supports 325, 330, suitable for receiving the filtration means represented by the numerical reference 116 in FIG. 1B. Said filter supports comprise several lugs 325 positioned in proximity to the openings 318, said lugs 325 extending as far as the level of the peripheral filter support 330, consisting of a collar. As previously indicated, the central element 31" also has a female clip-fastening element (not represented in FIG. 10), comprising two grooves hollowed out by reaming in the internal side wall 329 of the central element 31"; these two grooves (not represented) being suitable for receiving, respectively, the reams 327 and 328 of the male clip-fastening element of the pouring spout 31', and thus allowing the elastic interlocking of the pouring spout 31' in the central element 31".

Figure 13A:
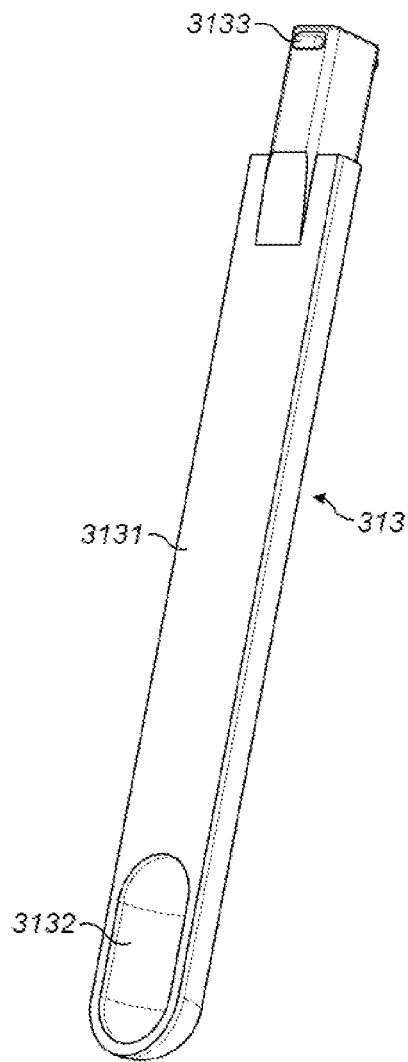
Figure 13B:
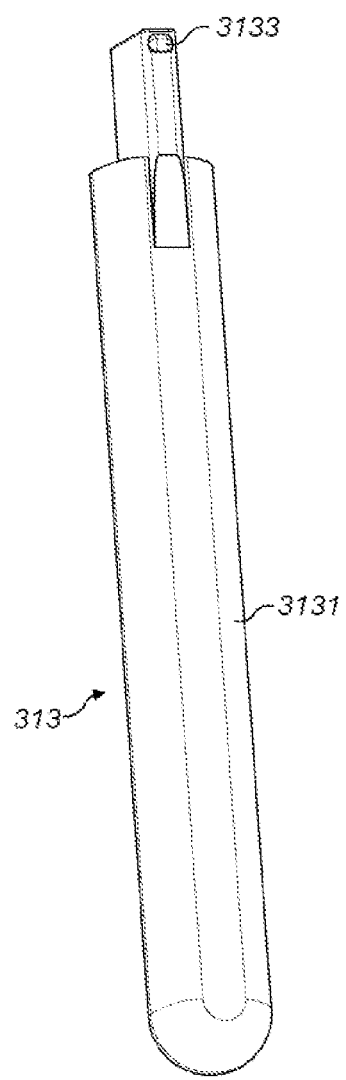

In addition, an opening 315 passes right through the central part of the central element 31". This opening 315 has a shape that is complementary to that of the male clip-fastening means 3133 of the sampling means 313, as represented in FIGS. 13A and 13B. More specifically, said opening 315 is trapezoidal in shape and is proportioned such that, when the male clip-fastening means 3133 of the sampling means 313 (cf. FIGS. 13A and 13B below) is plugged into the opening 315, the sampling means 313 is:
  (i) immobilized, and also
  (ii) oriented relative to the anti-rotation means 3201, 3202, as explained previously, in order to impose the desired orientation on the calibrated hollow part 3132 (cf. above).

Furthermore, the complementarity between, on the one hand, the shape of the opening 315 and, on the other hand, that of the male clip-fastening means 3133 imposes and guarantees the desired orientation of the sampling means 313—and in particular of its hollow part 3132—during the operation of assembling the sampling means 313 with the central element 31". In addition, the elastic interlocking of the part 3133 of the sampling means 313 in the opening 315 makes it possible to confer on the "central element 31"— sampling means 313" assembly, sufficient rigidity so that the rod 3131 of the sampling means 313 does not curve during the taking of sample with a heterogeneous matrix, avoiding, by the same token, the risks of projection of sample with a heterogeneous matrix.

The openings 318 as represented in FIG. 10 allow the passage of the suspending solution 13 loaded with sample with a heterogeneous matrix of the container 10 to the intermediate part 340 of the central element 31", containing the filtration means 116.

Although the assembly of the pouring spout 31' with a central element 31" and of the latter with the sampling means is obtained by elastic interlocking of male (327, 328 and 3133) and female (grooves hollowed out in the internal side wall 329 and opening 315) clip-fastening systems, the assembly of these various elements can, quite obviously, be obtained, alternatively, by any connecting/fixing system known to those skilled in the art, such as a screwing system, adhesive-bonding or else welding (for example heat-sealing).

Figure 11:
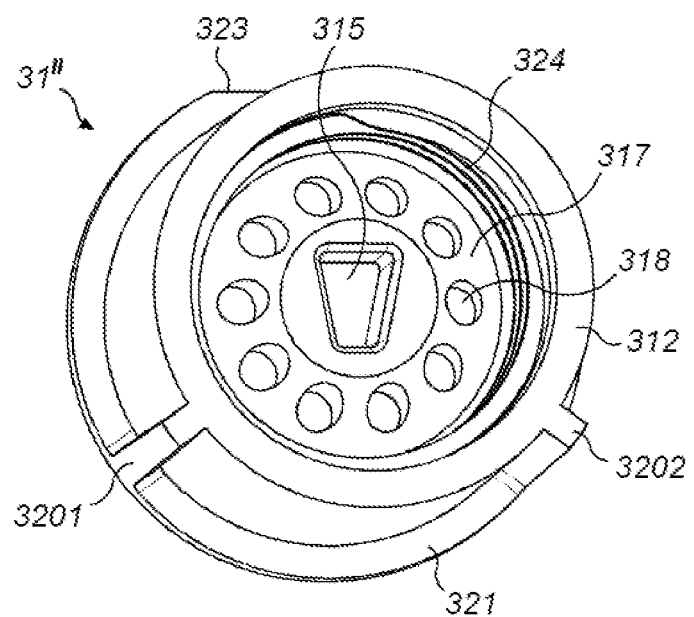
FIG. 11 represents a perspective view of the lower plane of the central part of the stopper represented in FIGS. 8A and 8B.

FIG. 11 represents a view from below, slightly in perspective, of the central part 31" of the stopper 31, on which the openings 318, arranged radially around the opening 315, are observed. By adjusting the relative placing of the trapezoidal opening 315 with respect to that of the anti-rotation means 3201, 3202, the hollow part 3132 of the sampling means 313 is oriented such that said hollow part is oriented downward, in order to promote the suspending of the sample with a heterogeneous matrix (as previously explained). In this FIG. 11, it is also noted that the internal part 317 has a truncated cone shape, making it possible to limit the risks of leakage of the suspension comprising the sample with a heterogeneous matrix. During the screwing of the stopper onto the container, said truncated cone-shaped part comes into contact with the edge of the container and crushes the angle of the edge of the container over a small surface area, thus ensuring good leaktightness.

Also observed in this FIG. 11 is an internal thread 324 obtained by tapping, intended to cooperate with an external thread made on the upper part of the container 10, preferably on the neck of the container 10, in order to allow the assembly of the stopper 31 and of the container 10 by screwing. Quite obviously, other closure systems, preferably hermetic closure systems, may be used to allow the assembly of the stopper and of the container, for example an elastic interlocking (clip-fastening) system.

Figure 12:
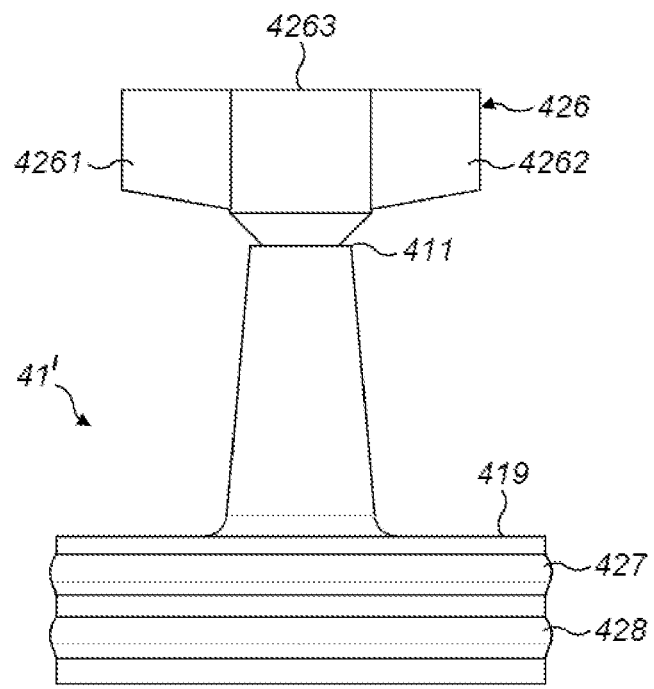
FIG. 12 represents a face-on view of a second embodiment of the pouring spout of the stopper represented in FIGS. 8A and 8B, FIGS. 13A and 13B represent two perspective views of the sampling means suitable for being connected to the stopper represented in FIGS. 8A and 8B.

FIG. 12 represents a second embodiment of the pouring spout 41' of the stopper according to the invention. This pouring spout 41' is suitable for being interlocked by elastic interlocking inside the central element 31" of the stopper 31. This is carried out by introducing the rings 427 and 428 into the corresponding grooves made in the internal side wall 329 of the central element 31" (cf. FIG. 10).

As shown in this FIG. 12, the tubular-shaped orifice 411 of this pouring spout 41' is rigidly connected to the breakable and repositionable cap 426 (for example, heat-sealed to said cap or simply molded at the same time as the cap, like conventional physiological saline pipettes), such that said breakable and repositionable cap 426 prevents, in this configuration, any uncontrolled exit of liquid via the tubular-shaped orifice 411, to the exterior.

In other words, when this breakable and repositionable cap 426 is rigidly connected to the tubular-shaped orifice 411, this makes it possible to prevent any uncontrolled leakage of liquid to the exterior of the device according to the invention. Furthermore, the fact that this breakable and repositionable cap 426 is rigidly connected to the tubular-shaped orifice 411 and closes the latter indicates to the operate that no liquid has previously been poured by the pouring spout 41'. The breakable and repositionable cap 427 thus indirectly acts as an impregnability control.

The breakable and repositionable cap 426 can be separated from the end of the tubular-shaped orifice 411 by the action of a force of tensile type or, preferably, twisting type on said breakable and repositionable cap 426, in particular by exerting a rotational force on one, or preferably even two, of the wings 4261 and 4262 of said cap 426.

The end of the breakable and repositionable cap 426, opposite the end in contact with the tubular-shaped orifice 411, comprises a hollow part 4263 of substantially cylindrical or truncated conical shape. This hollow part 4263 has a shape complementary to that of the end of the tubular-shaped orifice 411, such that, when the breakable and repositionable cap 426 is separated from the tubular-shaped orifice 411, for example by applying a tensile force to one, or even two, of the wings 4261 and 4262 of said cap 426, the latter can be used, subsequently, to again close the tubular-shaped orifice 411 of the pouring spout 41'. This closure is obtained by interlocking of the tubular-shaped orifice 411 in the hollow part 4263 of the breakable and repositionable cap 426.

It should be noted that, according to a simpler embodiment, the breakable and repositionable cap 426 can be replaced with a simple protective breakable part, which does not make it possible to reblock the tubular-shaped orifice 411 after separation of the protective breakable part thereof, contrary to the breakable and repositionable cap 426, represented in FIG. 12.

FIGS. 13A and 13B represent, respectively, a perspective view of three quarters of the calibrated sampling means 313 and a back view of this same calibrated sampling means 313. These two FIGS. 13A and 13B make it possible to observe the male clip-fastening means 3133, the rod made of solid material 3131 and the oblong-shaped calibrated hollow part 3132 (having more specifically a "stick" shape), said calibrated hollow part 3132 having been obtained by hollowing out a region located at the end of the rod 3131 opposite the internal part of the stopper (not represented in FIGS. 13A and 13B).

A second embodiment of the hollow part 4132 is represented diagrammatically in FIG. 14. On this face-on view, it is noted that said calibrated hollow part 4132 comprises openings 41321, intended to facilitate the suspending of the sample with a heterogeneous matrix present at the level of the calibrated hollow part 4132. This advantageous technical effect is obtained by allowing the suspending solution 13 to pass through the calibrated hollow part 4132 during the sample-suspending step. A calibrated hollow part 4132 according to this second embodiment proves to be particularly suitable for facilitating the suspending of samples with a heterogeneous matrix having significant adhesive properties, such as stools having a Bristol type 1 or 2.

FIG. 15 illustrates a third embodiment of the calibrated hollow part 5132 having ovoid-shaped openings 51321 with dimensions greater than those of the openings 41321 represented diagrammatically in FIG. 14. These openings 51321 make it possible to further facilitate the suspending of a sample with a heterogeneous matrix contained within the calibrated hollow part 5132. The hollow part 5132 according to this third embodiment proves to be particularly suitable for allowing the suspending of sample having adhesive properties that are more marked than those of the sample with a heterogeneous matrix that must be taken by means of or via the calibrated hollow part 4132 of FIG. 14, such as stools having a Bristol type 1-2.

FIG. 16 represents one particular embodiment, in which the sampling means 613 comprises, on a large part of its rod 6131, three square-shaped or rectangular-shaped calibrated hollow parts 6132, 6134 and 6135, each having a predetermined volume so as to allow each of these three calibrated hollow parts 6132, 6134 and 6135 to sample a mass of 1000 mg. The calibrated sampling means 613, represented in FIG. 16, thus makes it possible to take a total mass of 3000 mg of sample with heterogeneous matrix. A calibrated sampling means 613 of this type can prove to be particularly important for recovering, in fine, a filtrate containing a concentration of biological material and/or biological information that is sufficient to allow their analysis, in particular in the case where the biological material and/or biological information sought is (are) known to be present in very small amount in the material with a heterogeneous matrix from which the sample is taken. This sampling means 613 can also be used, advantageously, in veterinary applications, by increasing, as required, the volume defined by each of the hollow parts 6132, 6134 and 6135.

According to one particular embodiment, the rod 6131 of the sampling means 613 has, on its face opposite that comprising the three calibrated hollow parts 6132, 6134 and 6135, three additional calibrated hollow parts. Preferably, these three additional calibrated hollow parts each make it possible to take a mass of sample with a heterogeneous matrix of approximately 1000 mg. Thus, this suitable sampling means comprising six calibrated hollow parts makes it possible to take a total mass of sample with a heterogeneous matrix of approximately 6000 mg of sample with a heterogeneous matrix.

As represented in FIGS. 17 to 20, according to another preferred embodiment of the invention, the rod 7131 of the calibrated sampling means 713 is connected to a sliding extension 8. This sliding extension 8 makes it possible to extend the length of the rod 7131 of said calibrated sampling means 713 to a first length of rod. This sliding extension 8 is positioned by a translation on the calibrated sampling means 713, which already comprises a calibrated hollow part 7132 (which can be seen in FIG. 20). When the sliding extension 8 is in "exit" position, namely making it possible to confer the abovementioned first length of rod (cf. FIGS. 17 and 18), the operator can more easily take a sample with a heterogeneous matrix, for example a stool sample, at the bottom of a narrow tube, by means of at least one calibrated hollow part 81, positioned at the level of the end of the sliding extension 8 furthest from the internal part of the stopper, while avoiding any contact between the stopper and the edges of said tube.

After the sample with a heterogeneous matrix has been taken, and as previously indicated, the calibrated sampling means 713 and the container are assembled in order to make it possible to suspend the sample with a heterogeneous matrix and, in doing so, to continue the process for obtaining biological material and/or information according to the invention. During this assembly operation, the sliding extension 8 in the "exit" position (first length of rod; cf. FIGS. 17 and 18) butts against the bottom of the container and, under the effect of the opposing resistance by the bottom of the container, the sliding extension 8 slides along the rod 7131, in the direction of the internal part of the stopper, to its "re-entry" position (second length of rod; cf. FIGS. 19 and 20), in order to allow the assembly of the stopper and of the container, for example by screwing the stopper onto a thread positioned on the neck of the container, as previously indicated.

Figures 17, 18, 19, 20:
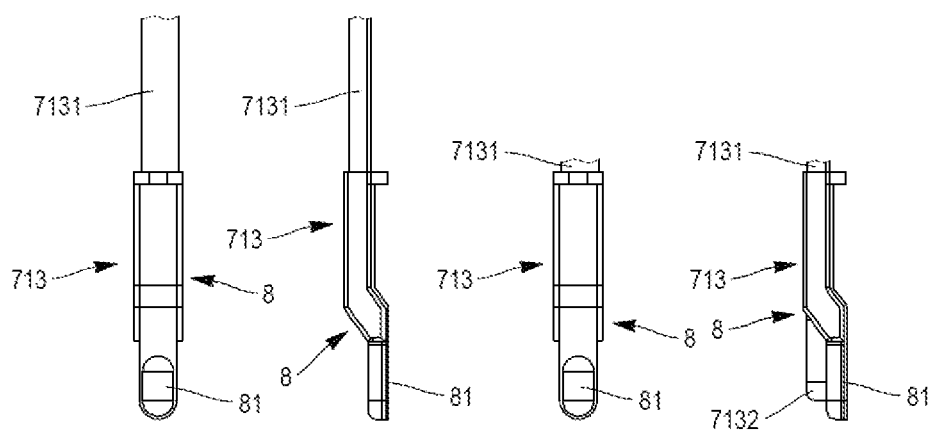
FIGS. 17 and 18 represent, respectively, a face-on view and a side view of a fifth embodiment of the calibrated sampling means according to the invention, comprising a sliding extension in the "exit" position, namely conferring on the rod a first length of rod, as previously described.
FIGS. 19 and 20 represent, respectively, a face-on view and a side view of the abovementioned fifth embodiment of the calibrated sampling means according to the invention, but in which the sliding extension is in the "re-entry" position, namely conferring on the rod a second length of rod, as previously described, less than the abovementioned first length of rod.

According to one embodiment of the invention, with a view to proceeding with the taking of sample with a heterogeneous matrix, the operator disassembles the stopper and the container, then slides the sliding extension 8 connected to the rod 7131 along the latter, from the "re-entry" position (second position; cf. FIGS. 19 and 20) to the "exit" position (first position; cf. FIGS. 17 and 18). According to one variant, in order to avoid any handling of the calibrated sampling means 713 prior to the sampling step (capable of generating microbial cross contamination), the stopper can be provided in a sterile packaging, the sliding extension 8 already in the "exit" position (first length of rod; cf. FIGS. 17 and 18). Thus, the sample with a heterogeneous matrix can be directly taken without the operator needing to touch the sliding extension 8.

Figure 21:
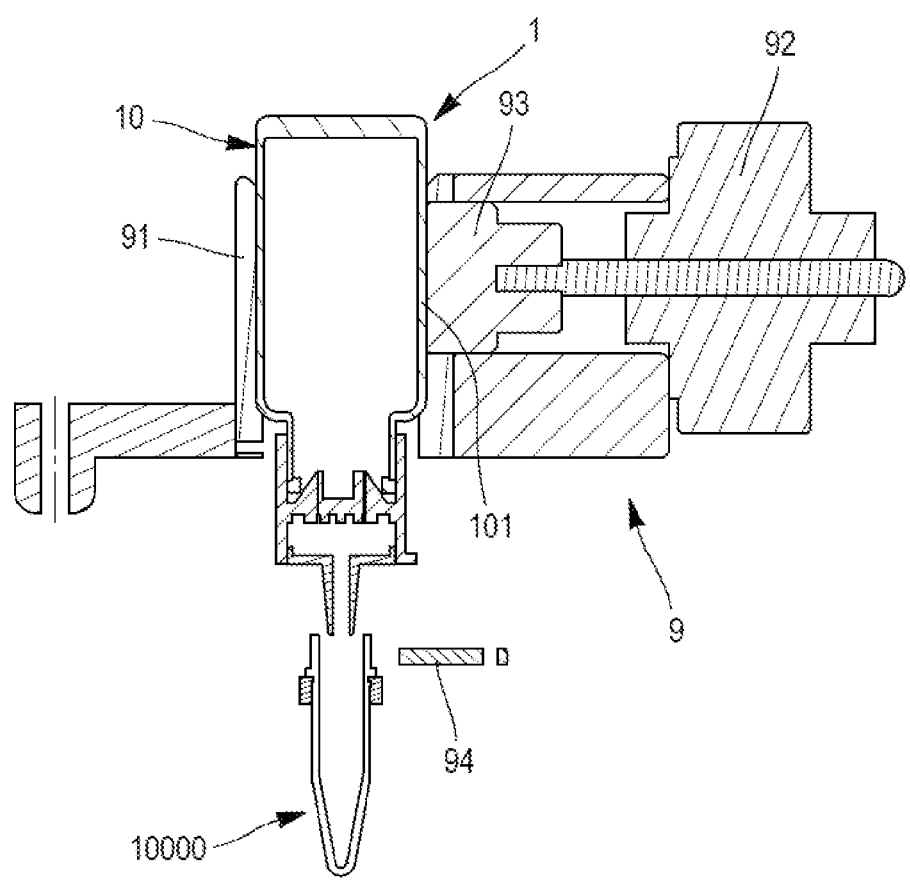
FIG. 21 is a sectional view of an automated filtration device according to the invention, suitable for allowing the automation of the step of filtration of the content (namely of the suspension containing the sample with a heterogeneous matrix of interest) from the device for obtaining biological material and/or biological information according to the invention.

As previously indicated, FIG. 21 is a sectional view of an automated filtration device 9 (or automatic filtration device) according to the invention. This automated filtration device makes it possible to automate the step of filtration of the content (namely of the suspension containing the sample with a heterogeneous matrix of interest) present within the device for obtaining biological material and/or biological information according to the invention.

The operator positions the device for obtaining biological material and/or biological information according to the invention 1 in a site 91 suitable for receiving and maintaining the device 1 during the filtration operation.

The operator then starts a motor 92 (for example by pressing on a push-button), which has the effect of causing a pressure member 93 to pass from an initial position ("resting position"—not represented in FIG. 21) to a "pressure" position (visible in FIG. 21), in which said pressure member 93 exerts a pressure against an area made of flexible material 101 of the container 10.

The pressure exerted by the pressure member 93 on said area made of flexible material 101 of the container 10 is maintained by virtue of the motor 92 for a period of time required to collect a desired volume of filtrate in a collecting receptacle 10000 (for example in an Eppendorf® tube).

The automated filtration device 9 particularly advantageously comprises an optical level detector 94 (also called "optical barrier"). This optical level detector 94 makes it possible to stop the filtration step when the desired level of filtrate is reached in the collecting receptacle 10000. More specifically, this optical detector operates by causing the pressure member 93 to pass from the pressure position to the resting position (under the action of the motor 92 or, more simply, by stopping the latter), namely stops the pressure exerted by the pressure member 93 on the area made of flexible material 101 of the container 10 when the optical level detector detects, via an optical sensor, that the desired level of filtrate is reached in the collecting receptacle 10000, thus ending the filtration step.

As previously explained, the fact that the pressure member 93 ceases to exert a pressure against said area made of flexible material 101 of the device 1 has the effect of ending the overpressure previously generated inside the container 10, thereby resulting in the filtration step being stopped when the desired level of filtrate is reached in the collecting receptacle 10000.

As mentioned above, the automated filtration device 9, provided with an optical level detector 94, proves to be particularly advantageous insofar as it makes it possible to collect the same volume of filtrate, whatever the type of stools, giving the process for obtaining biological material and/or biological information using the device 1 according to the invention repeatability and robustness. This is especially true, as previously explained, given that the calibrated hollow part of the device 1 according to the invention makes it possible to take a given/predefined mass of sample with a heterogeneous matrix (without having to perform weighing operations), said mass being constant or virtually constant at each operation of taking a sample with a heterogeneous matrix. In other words, said calibrated hollow part and the automated filtration device 9 according to the invention, provided with an optical level detector 94, act in synergy in order to guarantee optimal repeatability and robustness of the process for obtaining biological material and/or biological information using the device 1 according to the invention.

Even though, in the interests of clarity, a single site 91 is represented on the automated filtration device 9 which is the subject of FIG. 21, this automated filtration device 9 optimally comprises up to eight or even ten different sites 91, thereby making it possible to simultaneously filter up to eight or even ten devices 1, this being with optimal repeatability and optimal robustness, as explained above.

Figure 22:
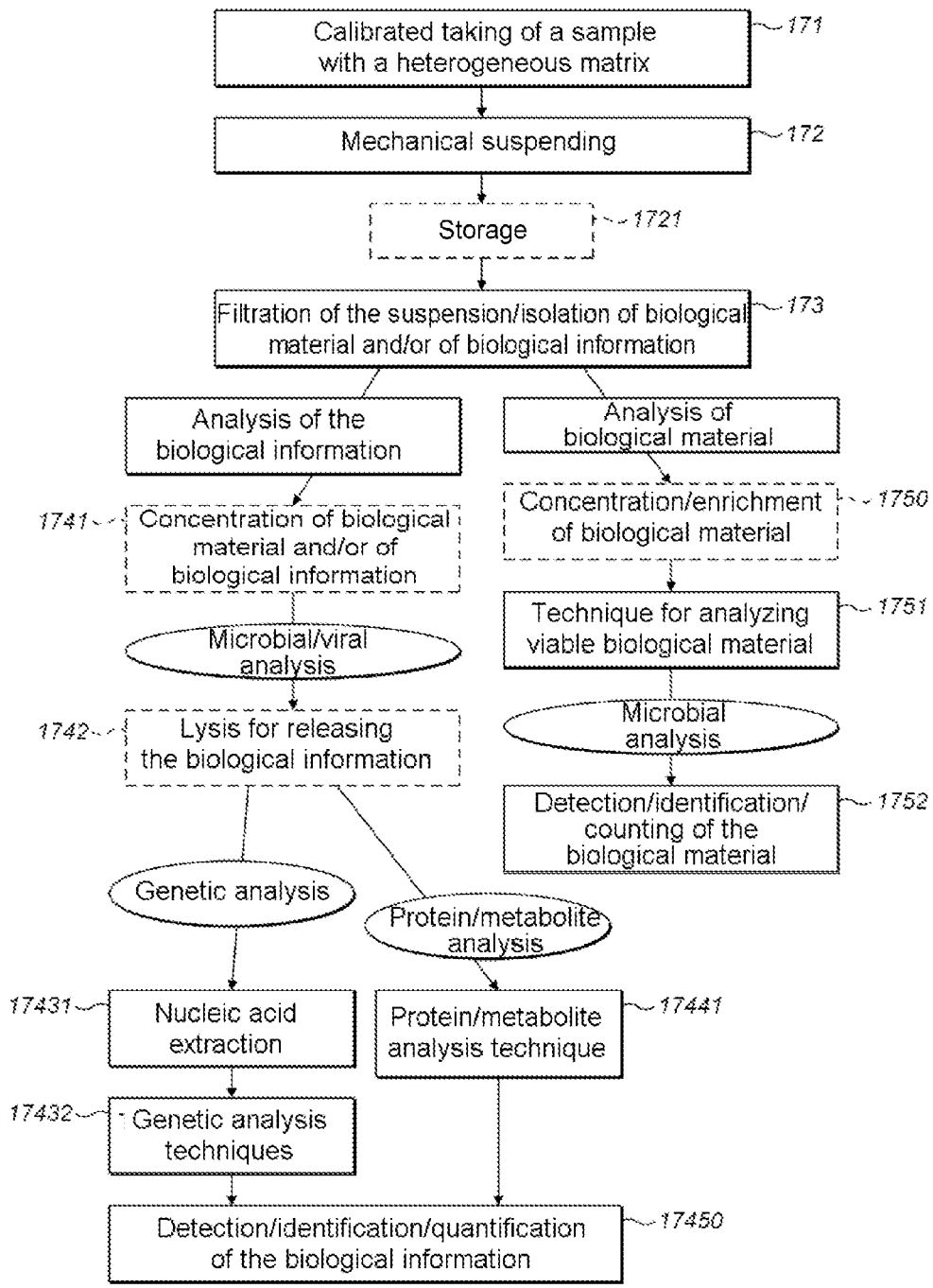
FIG. 22 is a diagram representing schematically the various steps of the processes for analyzing biological information and biological material according to the present invention.

FIG. 22 is a diagram representing:
(i) the various essential (solid line) and optional (dashed line) steps of the process for obtaining biological material and/or biological information according to the invention,
(ii) the various necessary (solid line) and optional (dashed line) steps of the various subsequent analysis pathways, allowing the identification and/or detection and/or quantification of said biological material and/or said biological information.

Steps 171, 712 and 173, represented on FIG. 22, are described in relation to the device 1, represented in FIGS. 1A and 1B.

In order to carry out the sampling step 171, the operator manually seizes the stopper, preferably by the stopper body, and fills the volume defined by the calibrated hollow part with the sample with a heterogeneous matrix (for example a stool sample). The stopper and the container, filled beforehand with a suspending solution, are assembled, for example by screwing the stopper onto the neck of the container, such that the sample with a heterogeneous matrix contained in the hollow part is in contact with the suspending solution.

It should be noted that the container may contain, in addition to the suspending solution, one or more suspending means, for example 30 glass beads, each having a diameter of 3 mm.

The suspending step 172 can be carried out by agitating the device in order to allow the suspending of the sample with a heterogeneous matrix contained in the calibrated hollow part in the suspending solution. In order to facilitate and/or accelerate this mechanical suspending step 172, the device can be connected to a mixing means, such as a vortex, as represented in FIG. 6. Advantageously, the device is connected to said mixing means by a maintaining member which closely cooperates with the rigid part of the stopper, in order to ensure effective maintaining of the device during the mechanical suspending step 172, consisting, in the case in point, of a mixing step.

Once the operator considers that the sample with a heterogeneous matrix has been correctly suspended in the suspending solution, the suspending step 172 is finished. At this time, the device containing the suspension of sample with a heterogeneous matrix can optionally be stored, in step 1721, preferably after addition of at least one preserving means and/or by freezing. Alternatively, the device can also be incubated at a temperature, for example at 37° C., for a period of a few hours to several days in order to enrich the suspension of certain microorganisms present in the sample. This incubation step can in particular be carried out in the presence of a selective culture means contained in the device according to the invention. The maximum duration of storage depends quite obviously on the preserving means used, where appropriate, and on the nature of the biological material and/or of the biological information to be analyzed. As previously indicated, this storage step can prove to be particularly advantageous in the context of operations for taking samples with a heterogeneous matrix "outside the laboratory". Indeed, the device optionally comprising a storage means can, after the tubular-shaped orifice has been closed by a cap, be sent to an analytical laboratory for the purpose of carrying out all the desired analyses of the biological material and/or of the biological information that may be contained in the sample with a heterogeneous matrix taken in step 171.

Alternatively, the operator can directly carry out the filtration step 173. In order to carry out this filtration step 173, the removable closure means is removed from the tubular-shaped orifice, then the device is subsequently turned upside down and at least one pressure is applied to at least one area of the flexible wall of the container, in order to create an overpressure in this container and thus to force the suspending solution loaded with sample with a heterogeneous matrix to pass through the filtration means of the stopper, via the openings. Thus, the suspending solution loaded with sample with a heterogeneous matrix which flows along the tubular-shaped orifice has necessarily been filtered by the filtration means 116 positioned in the body of the stopper. At the end of this filtration step 173, the filtrate containing said biological material and/or biological information is poured, via the tubular-shaped orifice, into a collecting tube, for example an Eppendorf tube. Once said biological material and/or biological information has (have) been isolated in the collecting tube, the operator can carry out various biological analyses, according to the nature of the biological material and/or biological information sought.

When it is desired to analyze the viable biological material, conventional microbiology techniques 1751 could be carried out for these purposes, such as the inoculating and culturing of said viable biological material on solid, liquid or semi-solid, selective or non-selective reaction media, preferably comprising a culture medium. The metabolic expression of this viable biological material can also be evaluated via the use of enzymatic tests (for example API strips, MALDI-TOF plate, lateral flow test). These microbiology techniques make it possible to detect and/or identify and/or count, in step 1752, the viable biological material sought. However, depending on the analysis techniques used, and on the type of viable biological material of interest, an additional step of enrichment may prove to be necessary in order to promote the growth of said biological material and thus to increase the concentration thereof in the reaction medium.

Quite obviously, said viable biological material, just like the biological information in the broad sense, can also be the subject of genetic, protein and/or metabolic analyses. To this effect, the reader will refer to the analysis of biological information, which is described hereinafter.

After the filtration step 173, when the operator wishes to analyze the biological information contained in the filtrate, and comprising in particular metabolites, proteins or else nucleic acids, specific detection and/or identification and/or quantification techniques are carried out.

Particularly advantageously, a step of concentrating said biological information 1741 contained in the filtrate is carried out by centrifugation at 6000-12 000 g of by flocculation, in order to concentrate the biological information of interest and to reduce the amount of non-targeted elements (such as inhibitors) present in the suspension. Where appropriate, a lysis step 1742 is carried out, when the biological information of interest is contained in said biological material, in particular when said biological material is a self-reproducible biological material, in order to make the biological information accessible to the analysis mean(s).

According to one variant, the lysis step 1742 can be carried out before the concentrating step 1741.

The subsequent steps depend on the nature of the biological information sought and on the analysis techniques used, genetic, protein or metabolic analysis techniques. When the operator wishes to analyze the biological information of interest by means of a genetic analysis technique (analysis of nucleic acid(s)), a nucleic acid extraction step 17431 is carried out by implementing any suitable nucleic acid extraction protocol. The nucleic acids obtained at the end of the extraction step 17431 are detected and/or identified and/or quantified by any appropriate genetic analysis method 174132, for example by PCR.

The protein and/or metabolic analysis 17441 involves, for its part, suitable analysis techniques, such as immunological assays (immunoassays) or else enzymatic assays (non-limiting list), which make it possible, in step 17450, to detect and/or identify and/or quantify the proteins and/or the metabolites of interest, initially present in the sample with a heterogeneous matrix.

The examples hereinafter will make it possible to understand the present invention more clearly. However, these examples are given only by way of illustration and should in no way be regarded as limiting the scope of said invention in any way.

EXAMPLES

Example 1—Assembly of a Device According to the Invention

For the purposes of example 1, the device for obtaining biological material and/or biological information from a sample with a heterogeneous matrix is assembled in the following way:
  inserting the first filter 1161 (Filtrona reference: BNW440148) into the central part of the central element 31" of the stopper 31,
  inserting a second filter 1162 (Pall Pad reference: 66025) in superimposition with respect to the first filter 1161,
  putting in place the pouring spout 41' by elastic interlocking of the male clip-fastening systems 427 and 428 and the female clip-fastening systems (grooves hollowed out in the internal side wall 329 of the central element 31"),
  clip-fastening the calibrated sampling means 313, having a calibrated hollow part 3132 (volume: 300 µl), in the opening 315 of the central element 31",
  adding 30 glass beads having a diameter of 3 mm to the container 10,
  adding 5 ml of suspending solution (in the case in point suspending buffer of TE buffer type) to the container 10, then
  screwing the stopper comprising the pouring spout 41' and the calibrated sampling means 313 onto the neck of the container 10.

Example 2—Process for Obtaining Biological Material and/or Biological Information Using the Device of Example 1

The protocol for obtaining biological material and/or biological information from a sample with a heterogeneous matrix according to the present invention, using the device described in example 1, comprises the following steps:

1) Taking the Sample

More specifically, the user firstly opens the pot containing the stools to be analyzed, and takes a sample using the calibrated sampling means 313, such that the calibrated hollow part 3132 of the calibrated sampling means 313 is filled with the sample of interest. In order to allow optimal calibration, the calibrated sampling means 313 is then "scraped" on the lip of the abovementioned pot in order to remove the possible surplus of salts present on the calibrated sampling means 313 and/or overflowing the calibrated hollow part 3132.

2) Suspending the Sample

Secondly, the user introduces the calibrated sampling means 313 into the container 10, and screws closed the stopper 31 before attaching the device according to the invention onto a mixing apparatus 71 (Genie II vortex; Scientific Industries, Inc.). More specifically, as represented in FIG. 6, the stopper of the device according to the invention is maintained by means of a clip 40 connected to a "vortex platform", itself placed on the mixing apparatus 71 ("vortex"). The device thus attached is mixed ("vortexed") until complete suspension of the sample is obtained, namely for a period of time generally of between 30 seconds and approximately 2 minutes depending on the Bristol type. Quite obviously, the optimal mixing ("vortexing") time for the sample may easily be determined by the user on the basis of their general knowledge and, where appropriate, of routine tests.

3) Filtering the Sample Suspended in Step 2)

In a third step, once the suspending step has been completed, the user removes the device according to the invention from the "vortex platform", then removes the cap 426 by applying a tensile force to the wings 4261 and 4262, turns the device upside down above a collecting tube (2 ml Eppendorf), then exerts a pressure with their fingers on the flexible walls 101 of the container 10 until the desired volume of filtrate is collected, namely approximately 2 ml. The filtrate thus obtained is ready to be analyzed.

Example 3—Efficiency of the Calibration of the Sampling Means 313 on Samples of Stools of Various Bristol Types The sampling is carried out using stool samples from healthy donors, stored at a temperature of −80° C. The stools are thawed beforehand.

The samplings are carried out by implementing step 1 of the process of example 2.

In order to accurately determine the mass of stools sampled in the calibrated hollow part 3132 of the sampling means 313, the stopper is weighed before (tare) and after the sampling operation.

The results obtained are presented in table 1 below:

TABLE 1

| Bristol | Bristol 2 | Bristol 3 | Bristol 3 | Bristol 4 | Bristol 5 | Bristol 6 |
|---|---|---|---|---|---|---|
| Weight of stools per sampling (mg) | 189 | 201 | 214 | 217 | 217 | 191 |
|  | 199 | 200 | 215 | 271 | 209 | 191 |
|  | 143 |  | 259 | 223 |  | 211 |
|  | 206 |  | 242 | 216 |  | 236 |
|  |  |  | 207 | 187 |  | 220 |
|  |  |  | 216 | 258 |  | 234 |
|  |  |  | 220 | 236 |  |  |
|  |  |  | 254 | 224 |  |  |
|  |  |  | 209 | 204 |  |  |
|  |  |  | 192 | 244 |  |  |
|  |  |  | 192 | 191 |  |  |
|  |  |  | 198 | 200 |  |  |
| Mean | 184 | 201 | 218 | 223 | 213 | 214 |
| CV (%) | 15 | 0.4 | 10 | 12 | 3 | 9 |

Example 3 makes it possible to calculate the sampling variability (CV), corresponding to all of the steps implemented in order to carry out the sampling.

The CV is a percentage calculated with respect to the standard error of the mean, by applying the following formula:

$$\sqrt{\frac{\sum (x - \bar{x})^2}{n}}$$

where x̃ the mean (number 1, number 2 . . . ) of the sample and n is the size of the sample.

The calibrated hollow part 3132 of the sampling means 313 makes it possible to collect a given/predetermined mass of stools easily, efficiently and reproducibly (robustness of the process for obtaining biological material and/or biological information using the device according to the invention), this being for various Bristol types. The minor variations in mass observed by repeatability are considered to be acceptable in that they do not significantly affect the amount of biological material and/or of biological information obtained by using the device.

Example 4—Test of Linearity of Detection of the Nucleic Acids of Various Types of Microorganisms Using the Process for Analyzing Biological Information According to the Invention In order to verify the efficiency of the process for analyzing biological information (in the case in point DNA) from a sample with a heterogeneous matrix, which is the subject of the present invention, the following three types of microorganisms were inoculated into the suspending solution contained in the device according to the invention:
carbapenem-resistant *Klebsiella pneumoniae* (KPC),
methicillin-resistant *Staphylococcus aureus* (MRSA),
*Schizosaccharomyces pombe* (*S. pombe*).

These three types of microorganisms were chosen according to their size and their characteristics, KPC being a Gram-negative *bacillus* 5 μm long, resistant to carbapenems, MRSA being a Gram-positive coccus 1 μm in diameter, resistant to methicillin, and *S. pombe* being a yeast 10 μm long and cylindrical in shape.

The inoculation of the suspending solution is prepared in the following way:
—MRSA and KPC MRSA and KPC are cultured on TSA (trypticase soy agar) overnight at 37° C. A solution of 7 McFarland corresponding to 2×10$^9$ CFU/ml (use of a densitometer) is prepared and diluted in cascade (1/10$^{th}$ dilutions) until the dilution 10$^3$ CFU/ml is obtained. 100 μl of the dilutions concerned are used to inoculate the suspending solution before the addition of the stool sample. 100 μl of the dilution at 10$^3$ CFU/ml are then deposited on COS dishes (reference: 43041, bioMérieux) (Columbia Agar+5% sheep blood) in triplicate in order to verify the concentration of the inoculant. The colonies are counted after 24 h of incubation (37° C.).
—*S. pombe*

*S. pombe* is cultured for two to three days on SDC agar (glucose Sabouraud agar; reference: 43555, bioMérieux) at 30° C., then overnight in a Sabouraud broth (30° C.) (reference: 42108, bioMérieux), the optical density is measured on a spectrophotometer and the broth is diluted in cascade until the dilution 10$^5$ CFU/ml is obtained. 100 μl of the dilutions concerned are used to inoculate the suspending solution before the addition of the stool sample. Direct counting of the yeasts under a microscope using a Kova cell is then carried out using the dilution at 10$^6$ CFU/ml in order to verify the concentration of the inocula.

Each suspending solution of each device is respectively inoculated with the following amounts of MRSA and of KPC: 0, 10$^5$, 10$^7$, 10$^8$ and 2×10$^9$ CFU. For *S. pombe*, the amounts inoculated are: 0, 10$^5$, 10$^6$ and 10$^7$ CFU.

Three controls are systematically carried out during the tests:
Negative control no. 1: device according to the invention, comprising a non-inoculated suspending solution (TE buffer) and a stool sample analyzed beforehand in order to be sure of the absence of MRSA, of KPC and of *S. pombe* in these stools,
Negative control no. 2: device according to the invention comprising a non-inoculated suspending solution (TE buffer), without stool sample, in order to verify that there have not been any contaminations during the manipulations,
Positive control: device according to the invention comprising a suspending solution (TE buffer) inoculated with all of the three microorganisms tested, at a known concentration, without stool sample, in order to determine the impact of the stools on the quantitative PCR detection of the microorganisms.

The following were added to the container 10: 5 ml of TE buffer and 30 glass beads having a diameter of 3 mm. The inoculation of the suspending solution is then carried out by adding 100 μl of the previously prepared suspensions. After inoculation, the device is used to carry out the sampling, suspending and filtration steps as described in example 2.

The sampling step 1) is carried out using a sample of stools from healthy donors, of stools stored in a pot and frozen at −80° C. The stools known to naturally contain KPC, MRSA or *S. pombe* were discarded.

The filtrate collected at the end of the filtration step 3) (cf. example 2) is centrifuged for 3 minutes at 12 000 g in order to concentrate the microorganisms. The supernatant is discarded and the pellet is resuspended in 600 μl of TE buffer by vortexing vigorously.

The 600 μl thus obtained are then transferred into a lysis tube (1.5 ml Eppendorf) prefilled with a mixture of beads consisting of 150 μg of zirconium beads 0.1 mm in diameter and 600 μg of glass beads 1 mm in diameter. The Eppendorf tube is subsequently placed on a "vortex platform" (24-position horizontal platform), itself placed on a Genie 2 vortex (Scientific Industries, Inc.), for 20 minutes and at maximum power, in order to lyse the microorganisms contained in the Eppendorf tube.

The solution thus lysed is recovered by pipetting and the beads are washed with 200 μl of TE buffer. The TE buffer that was used to wash the beads is recovered and added to the solution previously recovered by pipetting.

The entire volume recovered is then separated into two aliquots, each aliquot being introduced into a tube containing 2 ml of easyMAG® lysis buffer (reference: 280134, bioMérieux) and 140 μl of easyMAG® silica (reference: 280133, bioMérieux). Each mixture is then placed in a well of an easyMAG® shuttle (bioMérieux). Specific protocol "B" is launched, including an "off-board" lysis and an elution in a volume of 50 μl. The 2×50 μl of eluate originating from one and the same device are mixed, after extraction, in one and the same tube.

The easyMAG® reagents and consumables are listed hereinafter:
Reference: 280134 NucliSENS® easyMAG® lysis buffer (4×1000 ml/bottle)
Reference: 280130 NucliSENS® easyMAG® extraction buffer 1 (4×1000 ml/bottle)
Reference: 280131 NucliSENS® easyMAG® extraction buffer 2 (4×1000 ml/bottle)
Reference: 280132 NucliSENS® easyMAG® extraction buffer 3 (4×1000 ml/bottle)
Reference: 280133 NucliSENS® easyMAG® magnetic silica (48×0.6 ml/flask)
Reference: 280135 NucliSENS® easyMAG® consumables
Reference: 280146 Tips for multipette.

After extraction, 5 μl of eluates are used to carry out a PCR analysis targeting each of the three microorganisms inoculated. The results are expressed in Cq (quantification cycle), which is directly linked to the concentration of DNA present in the amplification tube as a function of the log of the concentration of microorganisms inoculated.

The primers and the probes used for the molecular analysis are specific for the KPC genes (gene encoding carbapenemases) in *K. pneumoniae*, for the SCCmec genes (methicillin resistance gene) in MRSA and for the SPBPJ4664.02 genes (glycoprotein) in *S. pombe*.

For each of the sequences of interest, the PCR mixes are prepared in accordance with the indications given in tables 2-4 below:

TABLE 2

PCR reagent mix for analysis of KPC

| Reagents | Final concentration |
|---|---|
| Acros water | — |
| Buffer pH 8.6 (X) | 1 |
| MgCl$_2$ solution (mM) | 3.5 |
| dNTP (mM) | 0.2 |
| BSA (μg/μl) | 0.5 |
| Antisense primer (μM) | 0.2 |
| Sense primer (μm) | 0.2 |
| Probe (μM) | 0.1 |
| DNA polymerase (Fast Start) (U/μl) | 0.08 |

TABLE 3

PCR reagent mix for analysis of *S. pombe*

| Reagents | Final concentration |
|---|---|
| Acros water | — |
| Buffer pH 8.6 (X) | 1 |
| MgCl$_2$ solution (mM) | 5 |
| dNTP (mM) | 0.2 |
| BSA (μg/μl) | 0.5 |
| Antisense primer (μM) | 0.65 |
| Sense primer (μm) | 0.65 |
| Probe (μM) | 0.17 |
| DNA polymerase (Fast Start) (U/μl) | 0.08 |

TABLE 4

PCR reagent mix for analysis of MRSA

| Reagents | Final concentration |
|---|---|
| Acros water | — |
| Buffer pH 8.6 (X) | 1 |
| MgCl$_2$ solution (mM) | 5 |
| dNTP (mM) | 0.2 |
| BSA (μg/μl) | 0.5 |
| Antisense primer (μM) | 0.2 |
| Sense primer (μm) | 0.2 |
| Probe (μM) | 0.1 |
| DNA polymerase (Fast Start) (U/μl) | 0.144 |

For each PCR reaction, the PCR reagent mixes are prepared in a final volume of 20 μl, to which are added 5 μl of the eluates obtained for each sample treated. The mixes are then amplified using a thermocycler, according to the amplification cycles presented in table 5 below:

TABLE 5

| | Enzymatic activation (Fast Start) | Denaturation | Hybridization/elongation |
|---|---|---|---|
| Temperature (° C.) | 95 | 95 | 65° C. |
| Time | 5 min | 15 sec | 45 sec |
| Cycle(s) | 1 | | 50 |

Figure 23:
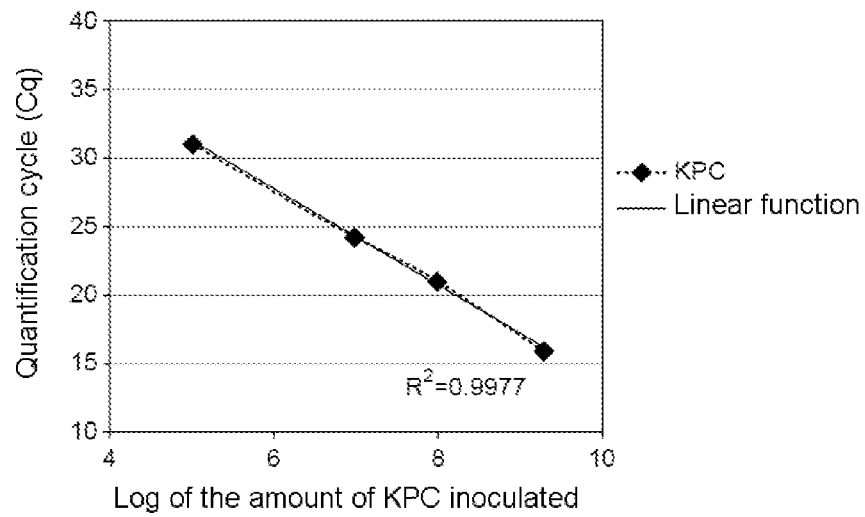
FIG. 23 is a graphic representation of the results obtained for a linearity test, quantifying the DNA (by PCR, Cq number) of Gram negative bacteria (KPC) by means of the process for analyzing biological information according to the invention, as a function of the log of the concentration of KPC inoculated. A linear regression ($R^2$) is represented and calculated (Linear)
Figure 24:
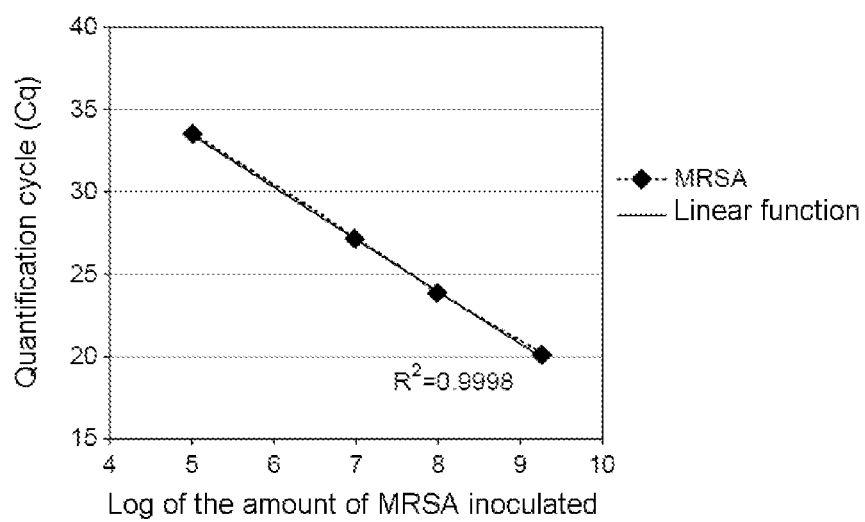
FIG. 24 is a graphic representation of the results obtained for a linearity test, quantifying the DNA (by PCR, Cq number) of Gram positive bacteria (MRSA) by means of the process for analyzing biological information according to the invention, as a function of the log of the concentration of MRSA inoculated. A linear regression ($R^2$) is represented and calculated (Linear)
Figure 25:
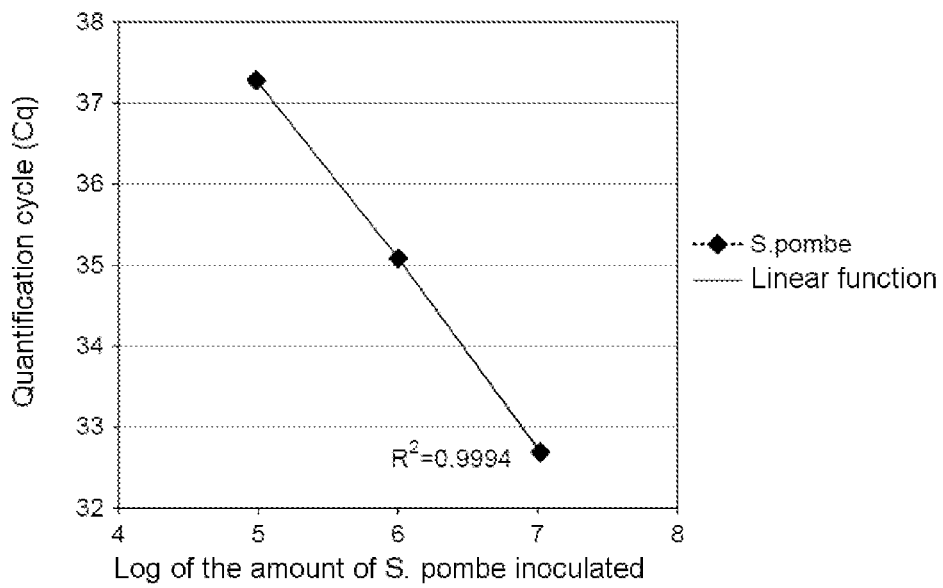
FIG. 25 is a graphic representation of the results obtained for a linearity test, quantifying the DNA (by PCR, Cq number) of *S. pombe* yeasts by means of the process for analyzing biological information according to the invention, as a function of the log of the concentration of the *S. pombe* inoculated. A linear regression ($R^2$) is represented and calculated (Linear), FIG. 26 compares the quantification by PCR of adenovirus DNA using the Adenovirus R-Gene® kit (reference: 69-010B) with the QIAamp® DNA stool extraction kit (QiaGen) and the process for extracting biological information according to the invention, FIG. 27 (on the left, scale in ng/µl, on the right in ratio) presents the impact of the Bristol type of the stools on the amount and the purity of the microorganism DNA extracted.

The results obtained (presented in FIGS. 23, 24 and 25) show a linear relationship between the amount of microorganisms previously inoculated into the suspending solutions and the amount of PCR-amplified DNA found in the eluate after extraction. Consequently, this demonstrates that the process for analyzing biological information according to the invention makes it possible to detect, in a "LOG-linear" manner, the microorganisms present in the stool samples, this being over the entire range of amounts tested.

In conclusion, in the light of the results thus obtained, it appears that the process for analyzing biological information according to the invention is efficient for isolating and identifying the microorganisms present in stool samples (including yeasts), both quantitatively and qualitatively.

Example 5—Comparison of the Process for Analyzing Biological Information According to the Invention and of the Protocol Using the QIAamp® DNA Stool Kit (QiaGen; Reference: 51504)

The inocula were prepared according to the methodology set out in example 4, from a solution at 0.5 McF corresponding to $10^8$ CFU/ml. The suspending solution is inoculated with $10^8$ CFU of MRSA, S. pombe and KPC. The control of the inocula is carried out as in example 4. The same is true for the negative controls no. 1 and no. 2 and of the positive control.

The obtaining and the quantification of the biological information are carried out by implementing the process for analyzing biological information (in the case in point DNA) according to the invention, described in example 4.

The obtaining of biological information with the QIAamp® DNA stool kit is carried out according to the experimental protocol provided by the supplier (QiaGen). Nevertheless, considering the present metagenomic application, a mechanical lysis step was added after addition of the ASL buffer and before incubation at 95° C. for 10 minutes, in order to obtain a better microorganism lysis yield. This is part of the general knowledge of those skilled in the art.

The biological information obtained using the QIAamp® DNA stool kit is quantified under the same conditions as those which make it possible to quantify the biological information obtained by implementing the process according to the present invention.

The results obtained for each of the two protocols are presented in table 6 below.

TABLE 6

Comparison of the results obtained by quantitative PCR using the DNA extracted by the process according to the invention and by the process according to the QIAamp ® DNA stool kit (QiaGen)

| Protocol | Amount of DNA extracted (µg) | qPCR result (Cq) | | |
|---|---|---|---|---|
| | | MRSA | KPC | S. pombe |
| Invention | 2.5-3 | 26.6 | 28.1 | 35.2 |
| QIAamp ® DNA stool | 7-10 | 28.4 | 29.2 | Not detected (>40) |

This table 6 presents the amount of DNA extracted for each of the two protocols, and also the value of the Cqs obtained by the PCR analysis (Cq corresponds to the Ct or threshold cycle, the cycle at which the emitted fluorescence value reaches the predefined threshold).

The results thus obtained clearly demonstrate that the molecular analysis of the biological information (DNA) by PCR, carried out using the eluates obtained by implementing the process according to the invention is efficient and exhibits improved sensitivity compared with the process using the QIAamp® DNA stool kit. In addition, it is important to note that only the process according to the invention makes it possible to detect yeasts (in this case, S. pombe yeasts).

In conclusion, the process for analyzing biological information according to the invention, using the device according to the invention, allows efficient detection of the biological information contained in the microorganisms present in a stool sample (including regarding yeasts), while at the same time simplifying the steps of sampling 1), suspending 2) and filtration 3) of the samples, as indicated in example 2.

Example 6—Comparison of the Process for Analyzing Biological Information According to the Invention and of the Process Using the QIAamp® DNA Stool Kit for a Human Organism Microbiota Sequencing Application The QIAamp® DNA stool kit (QiaGen; reference: 51504) is used in accordance with the experimental protocol provided by the supplier (QiaGen) and modified as mentioned in example 5 above.

The devices which are the subject of the present invention are assembled in accordance with the indications given in example 1. The filtrate is collected in accordance with example 2 and the DNA is extracted according to the extraction process according to the invention.

The filtrate treatment protocol is identical to that mentioned in example 3 for genetic material. However, the eluate thus obtained is then sequenced using a new-generation PGM sequence (IonTorrent) with a 318 chip (reference: see table 7 below).

TABLE 7

Reagents/kits used for sequencing the microbiota

| Reagents/kits | Storage | Supplier | Ref. | Batch |
|---|---|---|---|---|
| Ion PGM Sequencing Supplies 400 | RT | Life Technologies | 4482003 | 057A03-13 |
| Ion PGM Sequencing Reagents 400 | −20° C. | Life Technologies | 4482004 | 057A03-13 |
| Ion PGM Sequencing Solutions 400 | +4° C. | Life Technologies | 4482005 | 057A03-13 |
| Ion 318 Chip v2 kit | RT | Life Technologies | 4484354 | P30756-1 |

In order to test the reproducibility of the protocol implementing the present invention, three repetitions per experimental condition were carried out so as to make it possible to calculate the sampling variability (CV), corresponding to all of the steps implemented by the protocol.

The CV was calculated over the 10 phyla predominantly present in the stools. The results, presented in table 8 below, show that the CVs are equivalent between the two protocols (10-14%), with however a strong variation in value between phylum for the same protocol (6-23% for the process according to the invention and 2-35% for QiaGen). Consequently, this experiment shows that the DNA analysis process according to the invention makes it possible to obtain results that are equivalent in terms of reproducibility, while at the same time being simpler to produce than the process according to the QIAamp® DNA stool kit.

TABLE 8

CV of the 10 phyla predominantly present in the stools

| Taxon No. | Rank | Taxon | QiaGen CV (%) | Process according to the invention CV (%) |
|---|---|---|---|---|
| 1239 | Phylum | Firmicutes | 2% | 1% |
| 976 | Phylum | Bacteroidetes | 15% | 6% |
| 201174 | Phylum | Actinobacteria | 2% | 21% |
| 1224 | Phylum | Proteobacteria | 12% | 13% |
| 508458 | Phylum | Synergistes | 6% | 15% |
| 544448 | Phylum | Tenericutes | 14% | 23% |
| 203691 | Phylum | Spirochaetes | 2% | 17% |
| 1117 | Phylum | Cyanobacteria | 35% | 5% |
| 1090 | Phylum | Chlorobi | 17% | 23% |
| 3201, 3202 66 | Phylum | Fusobacteria | 22% | 17% |
|  |  | Mean | 13% | 14% |
|  |  | CV (CV variation) | 82% | 55% |

Example 7—Comparison in Terms of Quantification of Adenovirus DNA by PCR Using the Adenovirus R-Gene® Kit (Reference: 69-010B) after DNA Extraction with a) the QIAamp® DNA Stool Extraction Kit and with b) the Process for Extracting Biological Information According to the Invention In order to verify the concentration of adenovirus contained in the samples tested, stools containing a known concentration of adenovirus ("positive stool") are diluted in a mixture of stools not containing adenovirus. The dilution of the positive stools is carried out in cascade to the following concentrations: $10^4$, $10^5$, $10^6$ and $10^8$ copies of virus per gram of stool. In the case of the stools containing adenoviruses, the Bristol types are generally between 4 and 7.

Controls are systematically carried out:
2 negative controls: non-inoculated stools detected as negative and non-inoculated phosphate EDTA buffer.

For the adenovirus DNA extraction according to the QIAamp® DNA stool kit (ref. 51504, QiaGen), the supplier's experimental protocol is followed.

The process for extracting biological information (adenovirus DNA) is described hereinafter.

The 1) stool sampling, 2) suspending and 3) filtration steps are carried out in accordance with the teaching of example 2, using, as suspending solution, a solution consisting of phosphate (0.2 M), EDTA (50 mM), pH 8.

The filtrate thus obtained is vortexed for a few seconds for the purposes of homogenization, and then 400 μl of homogenized filtrate are subsequently transferred into the wells of an easyMAG® shuttle (bioMérieux) and the "Dispense Lysis" program is launched in order to distribute 2 ml of lysis buffer (bioMérieux, reference: 280134).

Once the "Dispense Lysis" program has ended, 10 μl of IC2 (internal control of the adenovirus R-Gene® kit), then 740 μl of a mixture, containing 600 μl of lysis buffer (bioMérieux, reference 280134) and 140 μl of silica, are added to each easyMAG® shuttle well. Once the mixture has been produced, the easyMAG® specific B, "off-board" lysis, program, elution in 50 μl, is launched. The eluate thus recovered is transferred into a new tube within 30 minutes following the end of the elution.

A quantitative PCR analysis is carried out in order to quantify the adenovirus DNA extracted according to, on the one hand, the process according to the invention and, on the other hand, the process according to the QIAamp® DNA stool process, as a function of the theoretical amount initially inoculated into the suspending buffer. Thus, 10 μl of eluates are taken to be analyzed by quantitative PCR using the adenovirus R-Gene® kit. The results are expressed in log of the concentration of microorganisms inoculated.

Figure 26:
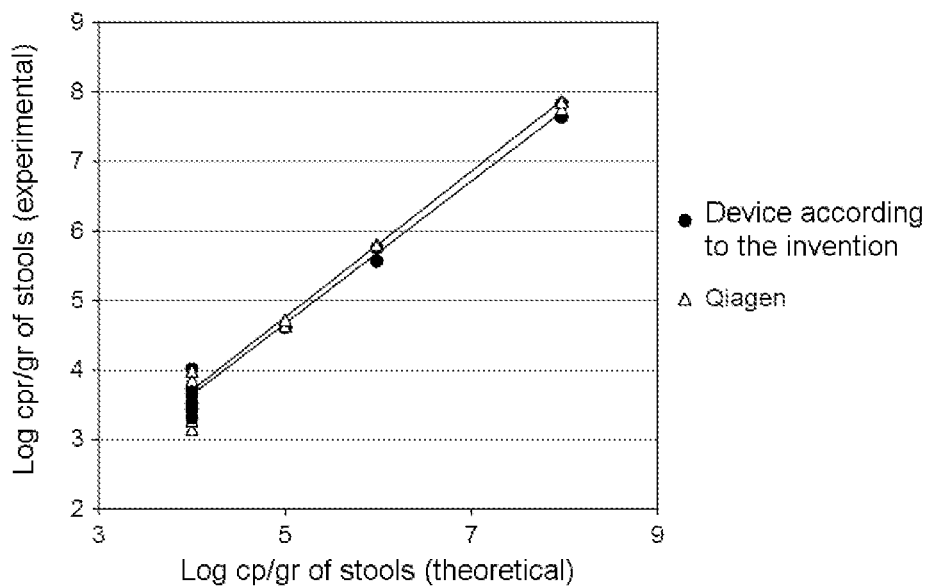

As shown by the results presented in FIG. 26, a linear relationship is noted between the number of viruses previously inoculated into the suspending buffer and the amount of DNA detected by quantitative PCR using the eluate obtained by implementing the process for extracting biological information according to the invention. Thus, the process for extracting biological information according to the invention (viral DNA) makes it possible to efficiently detect and quantify the adenoviruses initially present in a stool sample, and to obtain a result that is equivalent to the extraction process using the QIAamp® DNA stool kit, this being over a wide range of linearity (from $10^4$ to $10^8$ copies of virus per gram of stool).

Example 8—Test Showing the Amount of DNA Extracted from Samples of Stools of Different Bristol Type by Implementing the Process for Extracting Biological Information According to the Invention In order to evaluate the inter-stool reproducibility in terms of amount of DNA extracted from samples of stools of different Bristol types, several nucleic acid extractions were carried out on six different stool samples, the Bristol type of which is between 1 and 6, by implementing the process for extracting biological information (in the case in point DNA) according to the invention.

The abovementioned process for extracting biological information according to the invention is identical to the process described in example 4 up to the step involving the easyMAG®. The eluates thus obtained are analyzed on a Nanodrop (ThermoScientific), in order to quantify and verify the purity (260/280 ratio and 260/230 ratio) of the DNA extracted.

Figure 27:
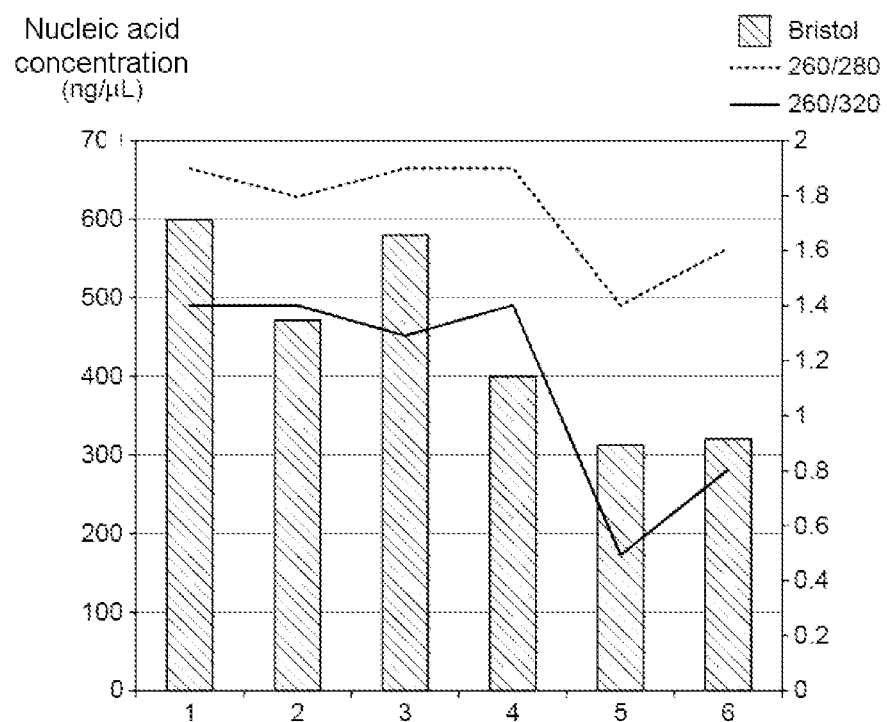

As illustrated in FIG. 27, a significant variation in the amount of DNA extracted is observed according to the Bristol type of the stool sample. Indeed, for stools of Bristol type 1 to 3, approximately 500 ng/μl of nucleic acids (5 μg of DNA) are extracted, while for stools of Bristol type 4 to 6, the nucleic acid concentration is close to 300 ng/μl nucleic acid (3 μg of DNA). The yield in terms of mass of DNA extracted is, consequently, approximately two times lower for the stools of Bristol type 4 to 6. However, the amount extracted remains sufficient to allow an analysis by PCR or by sequencing.

This variation in terms of amount of DNA extracted is not due to the nature of the extraction process used, but is clearly due to the Bristol type of the stools. Indeed, a DNA extraction carried out using the Macherey Nagel kit (NucleoSpin Blood L), adapted for DNA extractions from liquid samples (for example from blood) is carried out on the stools of Bristol type 5 and 6, and gives similar results (results not represented). This phenomenon is explained by the fact that the stools of Bristol type 5 and 6 are more liquid—and thus by definition more dilute—which results in a decrease in the concentration of microorganisms and thus, de facto, in their DNAs.

In conclusion, the process for extracting biological information (in the case in point DNA) according to the invention, using the device according to the invention, makes it possible to extract a sufficient amount of DNA from microorganisms in stools of Bristol type 1 to 6 to allow a subsequent analysis by PCR or sequencing, this being despite the variations observed in FIG. 27.

It should be noted that the process for extracting biological information (in the case in point DNA) according to the invention, using the device according to the invention, also works for stools of Bristol type 7; the absence of results for this Bristol type being simply due to the non-availability of stools of Bristol type 7 at the time this example was carried out.

Example 9—Test Demonstrating the Efficiency of the Device According to the Invention for Taking and Analyzing Bovine Stool Samples The taking and analyzing of a bovine stool sample are carried out by means of the device of which the assembly is described in example 1, with the exception that:

the calibrated sampling means 613 (comprising three calibrated hollow parts 6132, 6134 and 6135) of the device represented in FIG. 16 is used, in order to collect 3000 mg of bovine stools, and the volume of the TE buffer is increased to 10 ml.

The device according to the invention was used as indicated in example 2 up to the filtration step inclusive.

The device according to the invention thus made it possible to obtain 2 ml of a bovine stool filtrate, this being without clogging (blocking) of the filters of said device.

In conclusion, with a few adjustments, the device according to the invention is entirely suitable for one or more veterinary application(s), for example in order to obtain all or part of the microorganisms present in a stool sample of animal origin, for example a bovine stool sample.

Example 10—Comparison of the Implementation Time and the Practicality of Use Between the Process for Extracting Biological Information According to the Invention and the QIAamp® DNA Stool Kit (QiaGen)

In order to compare the implementation time and the practicality of use between the process for extracting biological information (in the case in point DNA) according to the invention and the protocol using the QIAamp® DNA stool kit, various DNA extractions were performed and the time for carrying out each step was reported in tables 9, 10 and 11 below, according to the type of process used.

The process using the QIAamp® DNA stool kit was used to treat five stool samples. A total of 25 manual steps (including 15 sample preparation steps) and a total duration of 2 h 20 (including 1 h 57 for the sample preparation) were required. The various steps of the process using the QIAamp® DNA stool kit and their implementation times are presented in table 9 below:

TABLE 9

| | | For 5 devices | |
|---|---|---|---|
| Item No. | Step of the "QIAamp ® DNA stool" process | Duration (h:min) | Cumulative duration (h:min) |
| 1 | Reagent and consumable preparation | 00:09 | |
| 2 | 200-250 mg stool sample taken | 00:10 | 00:10 |
| 3 | Lysozyme preparation | 00:10 | 00:20 |
| 4 | Lysozyme addition | 00:06 | 00:26 |
| 5 | Incubation 37° C. | 00:30 | 00:56 |
| 6 | Addition ASL + vortex 15 s/sample | 00:05 | 01:01 |
| 7 | Addition beads + Vibrobeating | 00:08 | 01:09 |
| 8 | Incubation 95° C. + preparation 2 ml tubes | 00:10 | 01:19 |
| 9 | Vortex 15s/sample. + centrifugation + transfer supernatant | 00:06 | 01:25 |
| 10 | Addition inhibitex + vortex + incubation RT | 00:04 | 01:29 |
| 11 | Centrifugation | 00:06 | 01:35 |
| 12 | Transfer supernatant + centrifugation | 00:05 | 01:40 |
| 13 | Preparation tubes + PK | 00:01 | 01:41 |
| 14 | Transfer supernatant + addition AL + homogenization | 00:04 | 01:45 |
| 15 | Incubation at 70° C. | 00:10 | 01:55 |
| 16 | Addition EtOH + vortex | 00:02 | 01:57 |
| 17 | Depositing on the column | 00:02 | 01:59 |
| 18 | Centrifugation | 00:02 | 02:01 |
| 19 | Addition AW1 + centrifugation | 00:02 | 02:03 |
| 20 | Addition AW2 + centrifugation | 00:04 | 02:07 |
| 21 | Addition AW2 + centrifugation | 00:05 | 02:12 |
| 22 | Addition AE | 00:01 | 02:13 |
| 23 | Incubation | 00:05 | 02:18 |
| 24 | Centrifugation | 00:01 | 02:19 |
| 25 | Preservation of eluate | 00:01 | 02:20 |

Moreover, the process for extracting biological information (in the case in point viral DNA and bacterial DNA) according to the invention was also carried out in order to also treat five stool samples.

The viral DNA extraction process according to the invention—for five samples—comprises eight steps (including three sample preparation steps) and is carried out in barely 1 h 30 (including 30 minutes of sample preparation). The various steps of the viral DNA extraction process and their implementation times are reported in table 10 below:

TABLE 10

| | | For 5 devices | |
|---|---|---|---|
| Item No. | Step of the "viral DNA" process | Duration (h:min) | Cumulative duration (h:min) |
| 1 | Reagent and consumable preparation | 00:14 | NA |
| 2 | Initiation of easyMAG ® | 00:13 | NA |
| 3 | 200-250 mg stool sample taken | 00:04 | 00:04 |
| 4 | Suspending | 00:05 | 00:09 |
| 5 | Filtration | 00:06 | 00:15 |

TABLE 10-continued

| | | For 5 devices | |
|---|---|---|---|
| Item No. | Step of the "viral DNA" process | Duration (h:min) | Cumulative duration (h:min) |
| 6 | Preparation easyMAG ® shuttle | 00:10 | 00:25 |
| 7 | Launch easyMAG ® protocol | 00:05 | 00:30 |
| 8 | Extraction in easyMAG ® | 01:00 | 01:30 |

The bacterial DNA extraction process—for five samples—comprises 12 steps (including seven sample preparation steps) and is carried out in 2 h 13 (including 58 minutes of sample preparation). The various steps of the bacterial DNA analysis process and their implementation time are reported in table 11 below:

TABLE 11

| | | For 5 devices | |
|---|---|---|---|
| Item No. | Step of the "bacterial DNA" process | Duration (h:min) | Cumulative duration (h:min) |
| 1 | Reagent and consumable preparation | 00:14 | NA |
| 2 | Initiation of easyMAG ® | 00:13 | NA |
| 3 | 200-250 mg stool sample taken | 00:04 | 00:04 |
| 4 | Suspending | 00:05 | 00:09 |
| 5 | Filtration | 00:06 | 00:15 |
| 6 | Centrifugation | 00:06 | 00:21 |
| 7 | Pellet taken up and resuspended | 00:12 | 00:33 |
| 8 | Mechanical lysis | 00:21 | 00:54 |
| 9 | Transfer supernatant | 00:04 | 00:58 |
| 10 | Preparation easyMAG ® shuttle | 00:10 | 01:08 |
| 11 | Launch easyMAG ® protocol | 00:05 | 01:13 |
| 12 | Extraction in easyMAG ® | 01:00 | 02:13 |

In the light of the data presented in tables 9, 10 and 11 above, it appears that the bacterial DNA and viral DNA extraction processes according to the invention, using the device of the invention, make it possible to limit the number of steps and to significantly reduce the sample preparation time.

Conversely, the process using the QIAamp® DNA stool kit requires a high number of manual and technically difficult steps, requiring the presence and continuous attention of a qualified laboratory technician.

In conclusion, the device according to the invention makes it possible to simplify the experimental protocols ("viral DNA" and "bacterial DNA") compared with the protocols of the prior art (QIAamp® DNA stool, QiaGen (ref. 51504)), by grouping together in one and the same device the elements required to carry out the sampling, suspending and filtration steps. This simplification makes it possible to significantly reduce the number and complexity of the manipulations, and to limit the risks of errors and of cross contaminations, while at the same time conferring increased working comfort for the normally qualified laboratory technician.

LITERATURE

{1} Srijan A. Bodhidatta I., Mason C, Bunyarakyothin G, Jiarakul W, Vithayasai N. Field Evaluation of a Transport Medium and Enrichment Broth for Isolation of *Campylobacter* Species from Human Diarrheal Stool Samples. J Med Microbiol, 2013; 3, 48-52.

[2] Wasfy M, Oyofo B, Elgindy A. Churilla A. Comparison of preservation media for storage of stool samples. J Clin Microbiol 1995; 33:2176.

The invention claimed is:

1. A device for obtaining biological material or biological information from a sample with a heterogeneous matrix, the device comprising: a container suitable for receiving a content comprising the sample and at least one suspending solution; and a stopper to close the container, the stopper comprising: at least one calibrated sampling element to take a predetermined volume of said sample corresponding to a given mass; at least one opening; and at least one filtration element for filtering the content when passed from the interior of the container to the exterior of the device via the at least one opening, wherein: the at least one calibrated sampling element comprises at least one calibrated hollow part connected to an internal part of the stopper; the at least one calibrated hollow part comprises at least one hollow part opening configured to facilitate suspending the sample in the suspending solution; the at least one filtration element is selected from: a. a gradient filter; and b. a superimposition of at least two filters, wherein the pore sizes of the at least two filters decrease in size from the most interior filter to the most exterior filter in the device; when the stopper and the container are assembled, the at least one calibrated sampling element extends from the internal part of the stopper to the interior of the container, and the at least one opening allows communication of fluid between the interior of the container and the exterior of the device; and the at least one filtration element is in a part of the stopper that is entirely external to the container when the stopper and the container are assembled so as to be closed.

2. The device as claimed in claim 1, wherein the content comprises the sample suspended in the at least one suspending solution.

3. The device as claimed in claim 1, wherein at least one mechanical suspending element is disposed within the container and configured to be moved by at least one force system external to the device.

4. The device as claimed in claim 3, wherein beads are the at least one mechanical suspending element and a mixing apparatus is the at least one force system.

5. The device as claimed in claim 3, wherein the at least one mechanical suspending element is spherical in shape.

6. The device as claimed in claim 5, wherein the at least one mechanical suspending element is selected from 1 to 200 beads.

7. The device as claimed in claim 6, wherein the 1 to 200 beads each have a diameter of between 2 mm and 10 mm.

8. The device as claimed in claim 7, wherein the 1 to 200 beads are made from a material selected from the group consisting of glass, iron, plastics, and ceramics.

9. The device as claimed in claim 1, wherein the at least one suspending solution is in a volume sufficient to suspend the sample.

10. The device as claimed in claim 1, wherein the container further comprises at least one wall, the wall comprising a flexible area suitable for undergoing compression to generate overpressure inside of the container to facilitate filtration of the content through the at least one filtration element.

11. The device as claimed in claim 1, wherein the at least one hollow part opening has a circular, ovoid, or elongated shape.

12. The device as claimed in claim 1, wherein the stopper further comprises at least one rigid area having a shape configured to cooperate with at least one maintaining member connected to a mixing apparatus so that the device is maintained on the mixing apparatus during mixing to facilitate the suspension of the sample in the suspending solution.

13. The device as claimed in claim 12, wherein the rigid area comprises one or more of:
   at least one anti-rotation element configured to prevent or stop rotation of the stopper; and
   at least one anti-translation element configured to prevent or stop a translational movement of the stopper.

14. The device as claimed in claim 1, wherein the calibrated hollow part is connected to the internal part of the stopper with a rod.

15. The device as claimed in claim 14, wherein the rod further comprises at least one sliding part, wherein the part is a sliding extension.

16. The device as claimed in claim 1, wherein the sample is selected from a soil sample, a human stool sample, an animal stool sample, a medico-legal sample, a food sample and an industrial sample.

17. A process for obtaining biological material or biological information from a sample with a heterogeneous matrix using a device, said process comprising:
   a) obtaining a predetermined volume of a sample corresponding to a given mass using a calibrated sampling element;
   b) suspending the sample in a suspending solution; and
   c) filtering the suspension obtained in step b) through a filtration element to obtain a filtrate containing the biological material or biological information,
   wherein the device is the device as claimed in claim 1.

18. The process of claim 17, further comprising
   d) lysing the biological material obtained in the filtrate in step c); and
   e) extracting the biological information from the lysate in step d).

19. The process of claim 17, further comprising concentrating the biological material or biological information after step a), b) and/or c).

20. A process for analyzing biological information comprising the following steps:
   i) extracting the biological information to be analyzed with the process of claim 17; and
   ii) identifying or quantifying the biological information by any appropriate method of analysis.

21. A process for analyzing biological information comprising the following steps:
   i) extracting the biological information to be analyzed with the process of claim 18; and
   ii) identifying or quantifying the biological information by any appropriate method of analysis.

22. A process for analyzing biological material from a sample with a heterogeneous matrix comprising the following steps:
   a) obtaining a filtrate with the process of claim 17; and
   d) analyzing the biological material by any appropriate element of biological analysis.

23. The process of claim 22, wherein the process further comprises between steps a) and d) the following steps:
   b) inoculating a reaction medium with the filtrate, the reaction medium being suitable for allowing the growth or expression of at least one metabolism of the biological material; and
   c) incubating the inoculated reaction medium.

24. The process of claim 22, wherein the step of analyzing the biological material comprises visual or optical reading of the material.

25. A kit for obtaining biological material or biological information from a sample with a heterogeneous matrix, the kit comprising:
   a) the device of claim 1; and
   b) at least one suspending solution.

26. The kit of claim 25, further comprising at least one mechanical suspending element.

27. The kit of claim 26, wherein the at least one mechanical suspending element comprises at least one bead.

28. A process for obtaining biological material or biological information from a sample with a heterogeneous matrix using a kit, such process comprising the following steps:
   a) taking a predetermined volume of sample corresponding to a given mass using a calibrated sampling element;
   b) suspending the sample in a suspending solution; and
   c) filtering the suspension obtained in step b) through a filtration element to obtain a filtrate containing the biological material or biological information,
   wherein the kit is the kit as claimed in claim 25.

29. The device as claimed in claim 1, wherein the at least one filtration element allows the selective passage of the biological material or biological information to the exterior of the device.

30. The device as claimed in claim 1, further comprising a removable closure element for removably closing the at least one opening.

31. The device as claimed in claim 13, wherein the rigid area has a shape configured to cooperate with a clip connected to said mixing apparatus, said clip comprising two ends, and wherein the at least one anti-rotation element comprises two distinct bearing surfaces and each of the two distinct bearing surfaces being suitable for butting against or coming into abutment against one of the two ends of the clip when the stopper undergoes a rotational movement.

32. The device as claimed in claim 31, wherein the two distinct bearing surfaces are two shoulders or two tabs.

33. The device as claimed in claim 13, wherein the rigid area has a shape configured to cooperate with a clip connected to said mixing apparatus, wherein the at least one anti-translation element comprises at least one bearing surface suitable for butting against or coming into abutment against said clip when the stopper undergoes a translational movement.

34. The device as claimed in claim 33, wherein the at least one bearing surface is selected from a lip, a collar and a shoulder.

35. A device for obtaining biological material or biological information from a sample with a heterogeneous matrix, the device comprising: a container suitable for receiving a content comprising the sample and at least one suspending solution; and a stopper to close the container, the stopper comprising: at least one calibrated sampling element to take a predetermined volume of said sample corresponding to a given mass; at least one opening; at least one filtration element for filtering the content when passed from the interior of the container to the exterior of the device via the at least one opening; and at least one rigid area having a shape configured to cooperate with at least one maintaining member connected to a mixing apparatus so that the device is maintained on the mixing apparatus during mixing to facilitate the suspension of the sample in the suspending solution, wherein: the at least one calibrated sampling element comprises at least one calibrated hollow part connected to an internal part of the stopper; the at least one calibrated hollow part comprises at least one hollow part opening configured to facilitate suspending the sample in the suspending solution; the at least one filtration element is selected from: a. a gradient filter; and b. a superimposition of at least two filters, wherein the pore sizes of the at least two filters decrease in size from the most interior filter to the most exterior filter in the device; when the stopper and the container are assembled, the at least one calibrated sampling element extends from the internal part of the stopper to the interior of the container, and the at least one opening allows communication of fluid between the interior of the container and the exterior of the device; and the at least one filtration element is in a part of the stopper that is entirely external to the container when the stopper and the container are assembled so as to be closed.

36. The device as claimed in claim 35, wherein the at least one hollow part opening has a circular, ovoid, or elongated shape.

37. The device as claimed in claim 36, wherein the hollow part is configured to contain a mass between 10 mg and 300 mg.

38. The device as claimed in claim 37, wherein each filter has a surface area greater than 50 mm$^2$.

39. The device as claimed in claim 38, wherein each filter has a surface area between 100 mm$^2$ and 350 mm$^2$.

40. The device as claimed in claim 39, wherein the rigid area comprises bearing surfaces configured to prevent the device from rotating while the device is maintained on the mixing apparatus during mixing.

41. The device as claimed in claim 40, wherein the bearing surfaces comprise shoulders or tabs.

42. The device as claimed in claim 40, wherein the rigid area comprises at least one bearing surface configured to prevent the device from undergoing translational movement while the device is maintained on the mixing apparatus during mixing.

43. The device as claimed in claim 42, wherein the at least one bearing surface comprises a lip, a collar, or a shoulder.

44. The device as claimed in claim 1, wherein the stopper hermetically closes the container.

45. The device as claimed in claim 1, wherein the calibrated hollow part is connected to the internal part of the stopper with a rod and the calibrated hollow part is a hollowed-out part on an external surface of the rod.

46. The device as claimed in claim 45, wherein the external surface of the rod is devoid of any other recess or cavity.

* * * * *